United States Patent
Chen

(10) Patent No.: US 8,513,283 B2
(45) Date of Patent: Aug. 20, 2013

(54) SPIRO SUBSTITUTED COMPOUNDS AS ANGIOGENESIS INHIBITORS

(75) Inventor: Guoqing Paul Chen, Moorpark, CA (US)

(73) Assignee: Advenchen Laboratories, LLC, Moorpark, CA (US)

( * ) Notice: Subject to any disclaimer, the term of this patent is extended or adjusted under 35 U.S.C. 154(b) by 1 day.

(21) Appl. No.: 13/411,874

(22) Filed: Mar. 5, 2012

(65) Prior Publication Data
US 2012/0165371 A1 Jun. 28, 2012

Related U.S. Application Data

(62) Division of application No. 12/036,245, filed on Feb. 23, 2008, now Pat. No. 8,163,923.

(60) Provisional application No. 60/894,693, filed on Mar. 14, 2007, provisional application No. 60/941,699, filed on Jun. 4, 2007.

(51) Int. Cl.
*A61K 31/04* (2006.01)

(52) U.S. Cl.
USPC .......................................................... 514/312

(58) Field of Classification Search
USPC .......................................................... 514/312
See application file for complete search history.

(56) References Cited

U.S. PATENT DOCUMENTS

| 7,560,558 | B2 | 7/2009 | Shimizu et al. | |
| 8,163,923 | B2 * | 4/2012 | Chen | 546/159 |
| 2006/0111375 | A1 | 5/2006 | Shimizu et al. | |
| 2008/0227811 | A1 | 9/2008 | Chen | |

FOREIGN PATENT DOCUMENTS

| WO | 2005044302 A1 | 5/2005 |
| WO | 2005063739 A1 | 7/2005 |
| WO | 2005073224 A2 | 8/2005 |
| WO | 2006071017 A1 | 7/2006 |

* cited by examiner

*Primary Examiner* — D M Seaman
(74) *Attorney, Agent, or Firm* — Rothwell, Figg, Ernst & Manbeck, P.C.

(57) ABSTRACT

The present invention relates to spiro (tetracarbon) substituted compound of Formula I, processes for their preparation, pharmaceutical compositions containing them as active ingredient, methods for the treatment of disease states associated with angiogenesis, such as cancers associated with protein tyrosine kinases, to their use as medicaments for use in the production of inhibition of tyrosine kinases reducing effects in warm-blooded animals such as humans.

Formula I

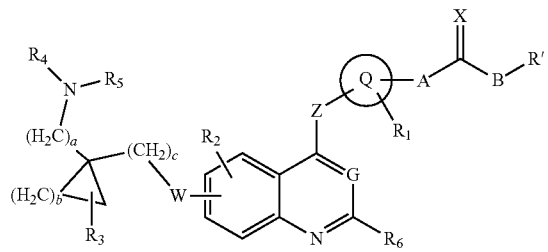

11 Claims, 3 Drawing Sheets

SPIRO SUBSTITUTED COMPOUNDS AS ANGIOGENESIS INHIBITORS

This application is divisional of U.S. Ser. No. 12/036,245 filed Feb. 23, 2008, which claims the benefit of U.S. Provisional Applications 60/894,693 filed on Mar. 14, 2007 and 60/941,699 filed on Jun. 4, 2007, the disclosure of which is incorporated herein in their entirety by reference.

FIELD OF THE INVENTION

The present invention relates to spiro (tetracarbon) substituted compounds, processes for their preparation, pharmaceutical compositions containing them as active ingredient, methods for the treatment of disease states associated with angiogenesis, such as cancers associated with protein tyrosine kinases, to their use as medicaments for use in the production of inhibition of tyrosine kinases reducing effects in warm-blooded animals such as humans.

BACKGROUND OF THE INVENTION

Receptor tyrosine kinases are large enzymes that span the cell membrane and possess an extracellular binding domain for growth factors, a transmembrane domain, and an intracellular portion that functions as a kinase to phosphorylate a specific tyrosine residue in proteins and hence to influence cell proliferation. Tyrosine kinases may be classified as growth factor receptor (e.g. EGFR, PDGFR, FGFR and erbB2) or non-receptor (e.g. c-src and bcr-abl) kinases. Such kinases may be aberrantly expressed in common human cancers such as breast cancer, gastrointestinal cancers such as colon, rectal or stomach cancer, leukemia, and ovarian, bronchial or pancreatic cancer. Aberrant erbB2 activity has been implicated in breast, ovarian, non-small cell lung, pancreatic, gastric and colon cancers.

Normal angiogenesis plays an important role in a variety of processes including embryonic development, wound healing and several components of female reproductive function. Undesirable or pathological angiogenesis has been associated with disease states including diabetic retinopathy, psoriasis, cancer, rheumatoid arthritis, atheroma. Tumor angiogenesis, the formation of new blood vessels and their permeability is primarily regulated by (tumor-derived) vascular endothelial growth factor (VEGF), which acts via at least two different receptors: VEGF-R1 (Flt-1); and VEGF-R2 (KDR, Flk-1). The VEGF KDR receptor is highly specific for vascular endothelial cells (*Endocr. Rev.* 1992, 13, 18; *FASEB J.* 1999, 13, 9).

A large number of human tumors, especially gliomas and carcinomas, express high levels of VEGF and its receptors. This has led to the hypothesis that the VEGF released by tumor cells stimulates the growth of blood capillaries and the proliferation of tumor endothelium in a paracrine manner and through the improved blood supply, accelerate tumor growth. Direct evidence of the role of VEGF as a tumor angiogenesis factor in vivo is shown in studies in which VEGF expression or VEGF activity was inhibited. This was achieved with anti-VEGF antibodies, with dominant-negative VEGFR-2 mutants which inhibited signal transduction, and with anti-sense-VEGF RNA techniques. All approaches led to a reduction in the growth of glioma cell lines or other tumor cell lines in vivo as a result of inhibited tumor angiogenesis.

Three principal mechanisms play an important part in the activity of angiogenesis inhibitors against tumors: 1) Inhibition of the growth of vessels, especially capillaries, into vascular resting tumors, with the result that there is no net tumor growth owing to the balance that is achieved between cell death and proliferation; 2) Prevention of the migration of tumor cells owing to the absence of blood flow to and from tumors; and 3) Inhibition of endothelial cell proliferation, thus avoiding the paracrine growth-stimulating effect exerted on the surrounding tissue by the endothelial cells which normally line the vessels.

The present invention is based on the discovery of compounds that surprisingly inhibit the effect of VEGF, a property of value in the treatment of disease states associated with angiogenesis and/or increased vascular permeability such cancer, diabetes, psoriasis, rheumatoid arthritis, Kaposi's, haemangioma, acute and chronic nephropathies, atheroma, arterial restenosis, autoimmune disease, acute inflammation, excessive scarformation and adhesions, lymphoedema, endometriosis, dysfunctional uterine bleeding and ocular diseases with retinal vessel proliferation.

It has now been found that spiro substituted compounds of formula I, described below, are a new class of compounds that have advantageous pharmacological properties and inhibit the activity of protein tyrosine kinases, such as VEGFr, EGFr, c-kit, PDGF, FGF, SRC etc. They may also be irreversible inhibitors of protein tyrosine kinases.

Examples of compounds that are similar in structure to those of the present invention are disclosed in the following literatures: WO9717329, WO9722596, WO0047212, WO2002032872, WO2004018430, WO2005073224, WO2005080377, WO2005097134, WO2005097137, WO2005114219, WO2005070891, WO05021553, WO2005063739.

SUMMARY OF THE INVENTION

The present invention relates to spiro substituted compounds of formula I

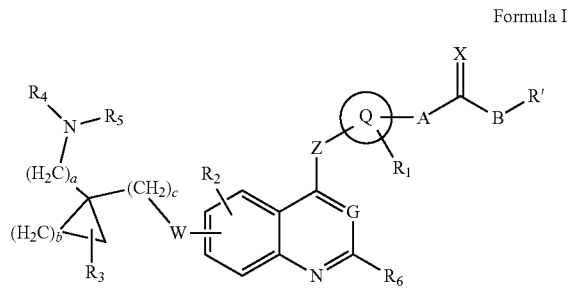

Formula I

Wherein
A is selected from direct bond or —N(R')—;
B is selected from direct bond, O, —N(R')—, —C(=X)— —C(=X)N(R')—, lower alkylenyl-C(=X)— or lower alkylenyl-C(=X)N(R')—;
X is selected from O or S;
R' is selected from H, halogen, halogeno-lower alkyl, lower alkyl, hydroxy, lower alkoxy, lower alkoxyalkoxy, lower alkenyl, lower alkynyl, amino, alkylamino, alkoxyamino, cycloalkyl, cycloalkenyl, aryl, lower aryl, heterocyclyl or lower heterocyclyl;
$R_1$, $R_2$ and $R_3$ are each independently selected from H, halogen, halogeno-lower alkyl, lower alkyl, hydroxy, lower alkoxy, lower alkoxyalkoxy, lower alkenyl, or lower alkynyl;
$R_4$ and $R_5$ are each independently selected from H, halogen, halogeno-lower alkyl, lower alkyl, hydroxy, lower alkoxy, lower alkoxyalkoxy, lower alkenyl, lower alkynyl, lower alkyl-OC(=O)—, ary-OC(=O)—, ary lower alkylenyl-OC(=O)—, lower alkyl-C(=O)—, ary-C(=O)—, ary lower alkylenyl-C(=O)—, lower alkyl-SO$_2$—, ary-SO$_2$—, ary lower alkylenyl-SO$_2$—, lower alkyl-C(=O)—, ary-C(=O)—, ary lower alkylenyl-C(=O)—, lower alkyl-N(R)C(=O)—, ary-N(R)C(=O)—, or ary lower alkylenyl-N(R)C(=O)—; R$_4$ and R$_5$ connect together to form a 3-8 membered saturated or unsaturated ring with their attached nitrogen;

R$_6$ is selected from H, halogen, halogeno-lower alkyl, lower alkyl;

W and Z are each independently selected from O, S, N—R or CH—R;

G is selected from C—R, C—(CN) or N;

a and c are each independently selected from 0, 1, 2, 3 or 4;

b is selected from 1, 2, 3, 4 or 5;

ring Q is a 5 to 13-membered monocyclic, bicyclic or tricyclic moiety which moiety may be saturated or unsaturated, which may be aromatic or non-aromatic, and which optionally may contain 1-3 heteroatoms selected independently from O, N and S;

or a pharmaceutically acceptable salt thereof.

DETAILED DESCRIPTION OF THE INVENTION

The present invention is the directed to novel compounds which can inhibit protein tyrosine kinase, and use of these compounds for inhibition of angiogenesis in the treatment of a neoplastic or proliferative or chronic inflammatory or angiogenic diseases which are caused by excessive or inappropriate angiogenesis in a mammal in need thereof.

In the compounds of formula I,

A is selected from direct bond or —N(R')—; preferably selected from direct bond or —NH—;

B is selected from direct bond, O, —N(R')—, —C(=X)—, —C(=X)N(R')—, lower alkylenyl-C(=X)— or lower alkylenyl-C(=X)N(R')—; preferably selected from —NH—, —C(=O)—, or —C(=O)NH—;

X is selected from O or S; preferably O;

R' is selected from H, halogen, halogeno-lower alkyl, lower alkyl, hydroxy, lower alkoxy, lower alkoxyalkoxy, lower alkenyl, lower alkynyl, amino, alkylamino, alkoxyamino, cycloalkyl, cycloalkenyl, aryl, lower alkylaryl, lower alkylheterocyclyl or heterocyclyl; preferably selected from H, halogen, halogeno-lower alkyl, lower alkyl, aryl, lower aryl, heterocyclyl or lower heterocyclyl;

R$_1$, R$_2$ and R$_3$ are each independently selected from H, halogen, halogeno-lower alkyl, lower alkyl, hydroxy, lower alkoxy, lower alkoxyalkoxy, lower alkenyl, or lower alkynyl; preferably selected from H, halogen, halogeno-lower alkyl, lower alkyl, hydroxy, lower alkoxy, lower alkoxyalkoxy;

R$_4$ and R$_5$ are each independently selected from H, halogen, halogeno-lower alkyl, lower alkyl, hydroxy, lower alkoxy, lower alkoxyalkoxy, lower alkenyl, lower alkynyl, lower alkyl-OC(=O)—, ary-OC(=O)—, ary lower alkylenyl-OC(=O)—, lower alkyl-C(=O)—, ary-C(=O)—, ary lower alkylenyl-C(=O)—, lower alkyl-SO$_2$—, ary-SO$_2$—, ary lower alkylenyl-SO$_2$—, lower alkyl-C(=O)—, ary-C(=O)—, ary lower alkylenyl-C(=O)—, lower alkyl-N(R)C(=O)—, ary-N(R)C(=O)—, or ary lower alkylenyl-N(R)C(=O)—; preferably selected from H, halogen, halogeno-lower alkyl, lower alkyl, lower alkoxy, t-butyl-OC(=O)—, benzyl-OC(=O)— or CH$_3$C(=O)—; R$_4$ and R$_5$ connect together to form a 3-8 membered saturated or unsaturated ring with their attached nitrogen; preferably R$_4$ and R$_5$ form a 4-6 membered ring with their attached nitrogen;

R$_6$ is selected from H, halogen, halogeno-lower alkyl, lower alkyl; preferably is H;

W and Z are each independently selected from O, S, N—R or CH—R; preferably W and Z selected from O or N—R;

G is selected from C—R, C—(CN) or N; preferably C—R or N a and c are each independently selected from 0, 1, 2, 3 or 4; preferably 0, 1 or 2;

b is selected from 1, 2, 3, 4 or 5; preferably 1, 2 or 3;

ring Q is a 5 to 13-membered monocyclic, bicyclic or tricyclic moiety which moiety may be saturated or unsaturated, which may be aromatic or non-aromatic, and which optionally may contain 1-3 heteroatoms selected independently from O, N and S; preferably ring Q is aryl or 9-10-membered heteroaromatic bicyclic moiety which contains 1-3 heteroatoms selected independently from O, N and S;

or a pharmaceutically acceptable salt thereof.

The term "halogen", as used herein, unless otherwise indicated, includes fluoro, chloro, bromo or iodo. such as fluoro and chloro.

The term "halogen-lower alkyl", as used herein, unless otherwise indicated, includes 1 to 6 halogen substituted alkyl, such as trifluoromethyl.

The term "lower alkyl", as used herein, unless otherwise indicated, includes 1 to 6 saturated monovalent hydrocarbon radicals having straight or branched moieties, including, but not limited to, methyl, ethyl, n-propyl, iso-propyl, n-butyl, sec-butyl, tert-butyl, and the like.

The term "lower alkenyl", as used herein, unless otherwise indicated, includes lower alkyl groups, as defined above, having at least one carbon-carbon double bond, such as —CH$_2$—CH=CH$_2$.

The term "lower alkynyl", as used herein, unless otherwise indicated, includes lower alkyl groups, as defined above, having at least one carbon-carbon triple bond, such as —CH$_2$—CH≡CH.

The term "lower alkoxy", as used herein, unless otherwise indicated, includes —O-lower alkyl groups wherein lower alkyl is as defined above, such as methoxy and ethoxy.

The term "lower alkoxyalkoxy", as used herein, unless otherwise indicated, includes —O-lower alkyl-O-lower alkyl groups wherein lower alkyl is as defined above, such as —OCH$_2$CH$_2$OCH$_3$.

The term "lower alkylenyl", as used herein, unless otherwise indicated, includes 1 to 6 saturated —CH$_2$— radicals.

The term "amino", as used herein, unless otherwise indicated, includes —NH$_2$ group, —NH-lower alkyl group, or —N(lower alkyl)$_2$ group wherein lower alkyl is as defined above, such as methylamine and dimethylamine.

The term "alkyamino", as used herein, unless otherwise indicated, includes -lower alkyl-NH$_2$ group, -lower alkyl-NH-lower alkyl group, or -lower alkyl-N(lower alkyl)$_2$ group wherein lower alkyl is as defined above, such as —CH$_2$CH$_2$NHCH$_3$.

The term "alkoxyamino", as used herein, unless otherwise indicated, includes —O-lower alkyl-NH$_2$ group, —O-lower alkyl-NH-lower alkyl group, or —O-lower alkyl-N(lower alkyl)$_2$ group wherein lower alkyl is as defined above, such as —OCH$_2$CH$_2$NHCH$_3$.

The term "aryl", as used herein, unless otherwise indicated, includes an organic radical derived from an aromatic hydrocarbon by removal of one hydrogen, such as phenyl or naphthyl, preferably phenyl, and is unsubstituted or substituted by one or two substituents, selected from halogen, halogeno-lower alkyl, lower alkyl, lower alkenyl, lower alkynyl, cyano, lower alkylcyano, hydroxy, lower alkoxy, carboxy, carboxyalkyl, amino, carbamoyl, cabamate, ureido, mercapto, sulfo, lower alkylsulfinyl, lower alkanesulfonyl, sulfonamide; aryl includes one aromatic ring fused with an aliphatic ring, such as a saturated or partially saturated ring, such as tetrahydronaphthyl.

The term "heterocyclyl", as used herein, unless otherwise indicated, includes non-aromatic, single and fused rings suitably containing up to four heteroatoms in each ring, each of which independently selected from O, N and S, and which rings, may be unsubstituted or substituted independently by, for example, up to three substituents. Each heterocyclic ring suitably has from 4 to 7, preferably 5 or 6, ring atoms. A fused heterocyclic ring system may include carbocyclic rings and need include only one heterocyclic ring which may be partially saturated or saturated. The heterocyclyl includes mono, bicyclic and tricyclic heteroaromatic ring systems comprising up to four, preferably 1 or 2, heteroatoms each selected from O, N and S. Each ring may have from 4 to 7, preferably 5 or 6, ring atoms. A bicyclic or tricyclic ring system may include a carbocyclic ring. Carbocyclic ring includes cycloalkyl, cycloalkenyl or aryl ring. examples of heterocyclyl groups include but not limited: azetidine, pyrrolidine, pyrrolidione, piperidine, piperidinone, piperazine, morpholine, oxetane, tetrahydrofuran, tetrahydropyran, imidazolidine, pyrazolidine and hydantoin, pyrrole, indole, pyrazole, indazole, trizole, benzotrizole, imidazole, benzoimidazole, thiophene, benzothiophene, thiozole, benzothiozole, furan, benzofuran, oxazole, bezoxazole, isoxazole, tetrazole, pyridine, pyrimidine, trizine, quinoline, isoquinoline, quinazoline, indoline, indolinone, benzotetrahydrofuran, tetrahydroquinoline, tetrahydroisoquinoline, methylene-dioxyphenyl. The heterocyclic and heterocyclic rings may be optionally substituted and substituents selected from the group defined above as substituents for aryl.

The term "cycloalkyl", as used herein, unless otherwise indicated, includes cyclic radicals having from three to eight ring carbon atoms, including, but not limited to cyclopropyl, cyclobutyl, cyclopentyl, cyclohexyl, and the like. The cycloalkyl groups may be optionally substituted one or more times, substituents selected from the group defined above as substituents for aryl, preferably halogen, lower alkyl.

The term "cycloalkenyl", as used herein, unless otherwise indicated, includes cycloalkyl groups, as defined above, having at least one carbon-carbon double bond.

The term "lower alkylaryl", as used herein, unless otherwise indicated, includes -lower alkyl-aryl group wherein lower alkyl and aryl are as defined above.

The term "lower alkylheterocyclyl", as used herein, unless otherwise indicated, includes -lower alkyl-heterocyclyl group wherein lower alkyl and heterocyclyl are as defined above.

Several in vitro tyrosine kinase inhibition activities can be measured according to the description in Rewcastle, G W, J. Med. Chem. 1996, 39, 918-928 and Edwards M, International Biotechnology Lab 5 (3), 19-25, 1987. Oncogene, 1990, 5: 519-524. The Baculovirus Expression System: A Laboratory Guide, L. A. King 1992. Sambrook et al, 1989, Molecular cloning—A Laboratory Manual, 2nd edition, Cold Spring Harbour Laboratory Press. O'Reilly et al, 1992, Baculovirus Expression Vectors—A Laboratory Manual, W. H. Freeman and Co, New York.

Receptor tyrosine kinase can be obtained in partially purified form from A-431 cells similar to those described by Carpenter et al., J. Biol. Chem., 1979, 254, 4884, Cohen et al., J. Biol. Chem., 1982, 257, 1523 and by Braun et al., J. Biol. Chem., 1984, 259, 2051. Some of these tests can also be contracted with Millipore Upstate Ltd for screening.

Compounds listed in examples have IC50 range from subnanomole to micromole inhibition activities towards various receptor tyrosine kinases. For example:

| Compound | Kinase | IC50 (nM) |
| --- | --- | --- |
| AL3810 | cKit(h) | 234 |
| AL3810 | c-RAF(h) | 293 |
| AL3810 | Flt1(h) | 4 |
| AL3810 | Flt4(h) | 2 |
| AL3810 | KDR(h) | 15 |
| AL3810 | PDGFRα(h) | 219 |

Animal antitumor activity testing can be conducted as follows:

The compounds were mixed with tween 80 and 0.5% CMC as suspensions. Nude female mice (17-19 g) were used. Ascitic fluid of human LOVO colon cancer (or mice HAC liver cancer) was diluted with 0.9% NaCl solution (1:4), and injected 0.2 ml to each mouse subcutaneously. The whole animals (n=12) were separated even as test and control group randomly. The test group was administered drugs orally at 0.5-500 mg/Kg dosage once a day from second day after injection of tumor for eighteen days. The animals were sacrificed at 21st days and each tumor was extracted and weighted for both groups and calculated the difference in percentage for antitumor activity.

The following are some activities showing on animal model with better efficacy than SU11248 and Nexavar:

BRIEF DESCRIPTION OF THE DRAWINGS

The figures show activity on animal models with AL3810 having better efficacy than SU11248 and Nexavar.

Figure 1:
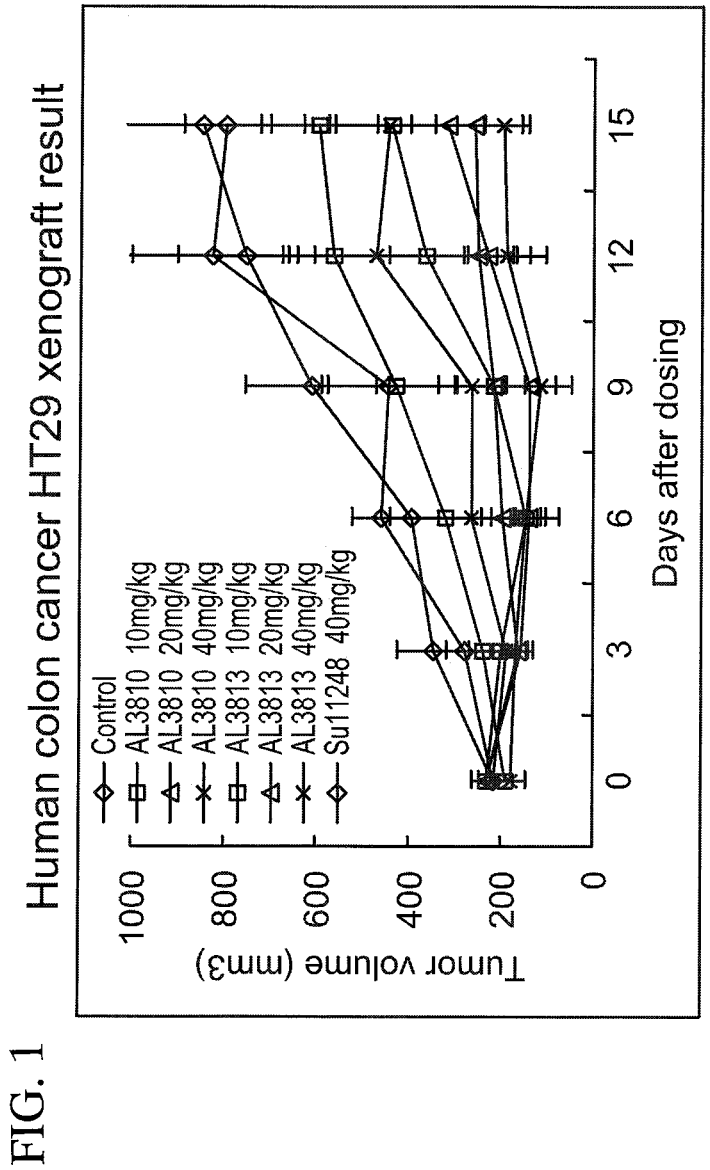
FIG. 1 shows the results obtained using AL3810 and Su11248 on a human colon cancer HT29 xenograft.
Figure 2:
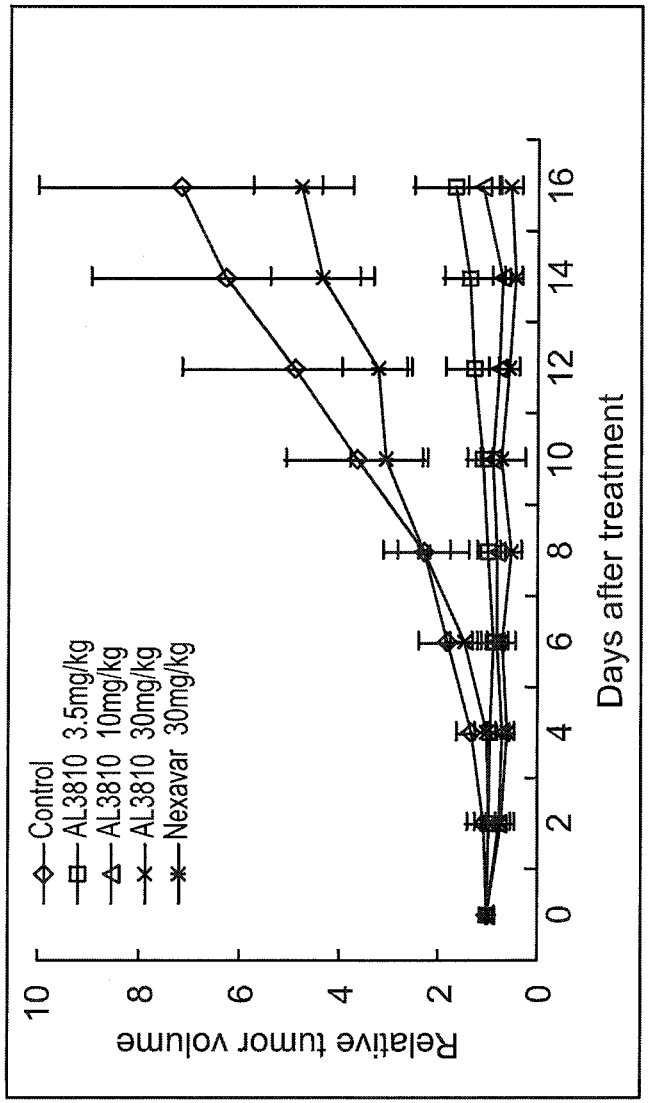
FIG. 2 shows the results obtained using AL3810 and Nexavar on a human liver cancer Bel-7402 xenograft.
Figure 3:
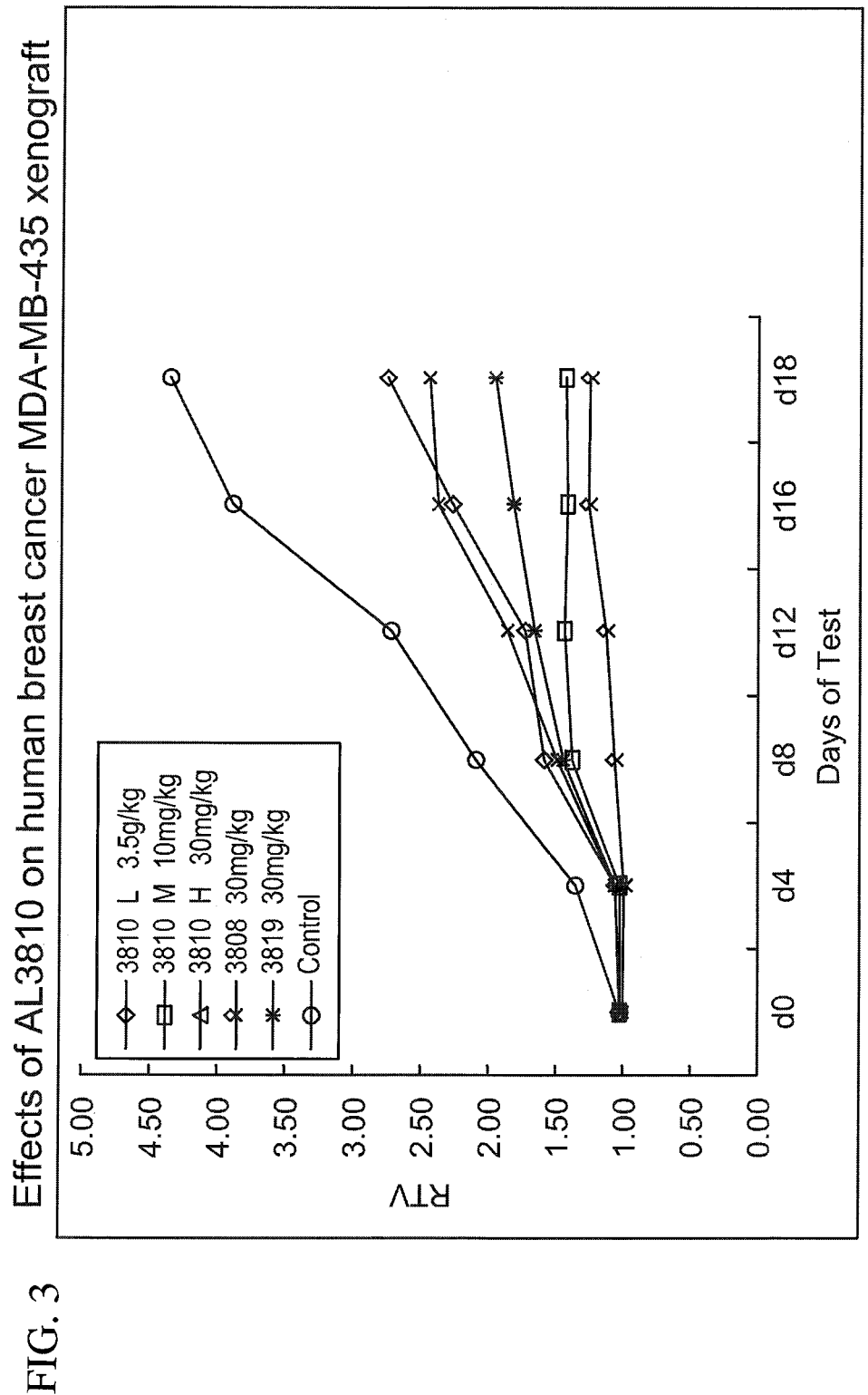
FIG. 3 shows the results obtained using AL3810 on a human breast cancer MDA-MB-435 xenograft.

A compound of present invention can be used in a method of treating cancer in a subject, said method comprising administering an effective amount of said compound.

A compound of present invention can be used in a method of treating angiogenesis in a subject, said method comprising administering an effective amount of said compound.

A compound of formula I can be administered alone or in combination with one or more other therapeutic agents, possible combination therapy taking the form of fixed combinations or administration of a compound of the invention and one or more other therapeutic agents being staggered or given independently of one another, or the combined administration of fixed combinations and one or more other therapeutic agents.

A compound of formula I can besides or in addition be administered especially for tumor therapy in combination with chemotherapy, radiotherapy, surgical intervention, or a combination of these. Long term therapy is equally possible as is adjuvant therapy in the context of other treatment strategies, as described above. Other possible treatments are therapy to maintain the patient's status after tumor regression, or even chemopreventive therapy, for example in patients at risk.

A compound according to the invention is not only for management of humans, but also for the treatment of other warm-blooded animals, for example of commercially useful animals. Such a compound may also be used as a reference standard in the test systems described above to permit a comparison with other compounds.

Salts are especially the pharmaceutically acceptable salts of compounds of formula I. Suitable pharmaceutically acceptable salts will be apparent to those skilled in the art and include those described in *J. Pharm. Sci.*, 1977, 66, 1-19, such as acid addition salts formed with inorganic acid e.g. hydrochloric, hydrobromic, sulphuric, nitric or phosphoric acid; and organic acids e.g. succinic, maleic, acetic, fumaric, citic, tartaric, benzoic, p-toluenesulfonic, methanesulfonic or naphthalenesulfonic acid. Other salts may be used, for example in the isolation or purification of compounds of formula (I) and are included within the scope of this invention.

The compounds of this invention may be in crystalline or non-crystalline form, and, if crystalline, may optionally be hydrated or solvated. This invention includes within its scope stoichiometric hydrates as well as compounds containing variable amount of water.

The invention extents to all isomeric forms including stereoisomers and geometric isomers of the compounds of formula (I) including enantimers and mixtures thereof e.g. racemates. The different isomeric forms may be separated or resolved one from the other by conventional methods, or any given isomer may be obtained by conventional synthetic methods or by stereospecific or asymmetric syntheses.

Those skilled in the art will recognize various synthetic methodologies that may be employed to prepare non-toxic pharmaceutically acceptable prodrugs of the compounds encompassed by Formula I. Those skilled in the art will recognize a wide variety of non-toxic pharmaceutically acceptable solvents that may be used to prepare solvates of the compounds of the invention, such as water, ethanol, mineral oil, vegetable oil, and dimethylsulfoxide.

The compounds of general Formula I may be administered orally, topically, parenterally, by inhalation or spray or rectally in dosage unit formulations containing conventional non-toxic pharmaceutically acceptable carriers, adjuvants and vehicles. Oral administration in the form of a pill, capsule, elixir, syrup, lozenge, troche, or the like is particularly preferred. The term parenteral as used herein includes subcutaneous injections, intradermal, intravascular (e.g., intravenous), intramuscular, spinal, intrathecal injection or like injection or infusion techniques. In addition, there is provided a pharmaceutical formulation comprising a compound of general Formula I and a pharmaceutically acceptable carrier. One or more compounds of general Formula I may be present in association with one or more non-toxic pharmaceutically acceptable carriers and/or diluents and/or adjuvants and if desired other active ingredients. The pharmaceutical compositions containing compounds of general Formula I may be in a form suitable for oral use, for example, as tablets, troches, lozenges, aqueous or oily suspensions, dispersible powders or granules, emulsion, hard or soft capsules, or syrups or elixirs.

Compositions intended for oral use may be prepared according to any method known to the art for the manufacture of pharmaceutical compositions and such compositions may contain one or more agents selected from the group consisting of sweetening agents, flavoring agents, coloring agents and preserving agents in order to provide pharmaceutically elegant and palatable preparations. Tablets contain the active ingredient in admixture with non-toxic pharmaceutically acceptable excipients that are suitable for the manufacture of tablets. These excipients may be for example, inert diluents, such as calcium carbonate, sodium carbonate, lactose, calcium phosphate or sodium phosphate; granulating and disintegrating agents, for example, corn starch, or alginic acid; binding agents, for example starch, gelatin or acacia, and lubricating agents, for example magnesium stearate, stearic acid or talc. The tablets may be uncoated or they may be coated by known techniques to delay disintegration and absorption in the gastrointestinal tract and thereby provide a sustained action over a longer period. For example, a time delay material such as glyceryl monosterate or glyceryl distearate may be employed.

Formulations for oral use may also be presented as hard gelatin capsules wherein the active ingredient is mixed with an inert solid diluent, for example, calcium carbonate, calcium phosphate or kaolin, or as soft gelatin capsules wherein the active ingredient is mixed with water or an oil medium, for example peanut oil, liquid paraffin or olive oil.

Aqueous suspensions contain the active materials in admixture with excipients suitable for the manufacture of aqueous suspensions. Such excipients are suspending agents, for example sodium carboxymethylcellulose, methylcellulose, hydropropylmethylcellulose, sodium alginate, polyvinylpyrrolidone, gum tragacanth and gum acacia; dispersing or wetting agents may be a naturally-occurring phosphatide, for example, lecithin, or condensation products of an alkylene oxide with fatty acids, for example polyoxyethylene stearate, or condensation products of ethylene oxide with long chain aliphatic alcohols, for example heptadecaethyleneoxycetanol, or condensation products of ethylene oxide with partial esters derived from fatty acids and a hexitol such as polyoxyethylene sorbitol monooleate, or condensation products of ethylene oxide with partial esters derived from fatty acids and hexitol anhydrides, for example polyethylene sorbitan monooleate. The aqueous suspensions may also contain one or more preservatives, for example ethyl, or n-propyl p-hydroxybenzoate, one or more coloring agents, one or more flavoring agents, and one or more sweetening agents, such as sucrose or saccharin.

Oily suspensions may be formulated by suspending the active ingredients in a vegetable oil, for example arachis oil, olive oil, sesame oil or coconut oil, or in a mineral oil such as liquid paraffin. The oily suspensions may contain a thickening agent, for example beeswax, hard paraffin or cetyl alcohol. Sweetening agents such as those set forth above, and flavoring agents may be added to provide palatable oral preparations. These compositions may be preserved by the addition of an anti-oxidant such as ascorbic acid.

Dispersible powders and granules suitable for preparation of an aqueous suspension by the addition of water provide the active ingredient in admixture with a dispersing or wetting agent, suspending agent and one or more preservatives. Suitable dispersing or wetting agents and suspending agents are exemplified by those already mentioned above. Additional excipients, for example sweetening, flavoring and coloring agents, may also be present.

Pharmaceutical compositions of the invention may also be in the form of oil-in-water emulsions. The oily phase may be a vegetable oil, for example olive oil or arachis oil, or a mineral oil, for example liquid paraffin or mixtures of these. Suitable emulsifying agents may be naturally-occurring gums, for example gum acacia or gum tragacanth, naturally-occurring phosphatides, for example soy bean, lecithin, and esters or partial esters derived from fatty acids and hexitol, anhydrides, for example sorbitan monoleate, and condensation products of the said partial esters with ethylene oxide, for example polyoxyethylene sorbitan monoleate. The emulsions may also contain sweetening and flavoring agents.

Syrups and elixirs may be formulated with sweetening agents, for example glycerol, propylene glycol, sorbitol or sucrose. Such formulations may also contain a demulcent, a preservative and flavoring and coloring agents.

The compounds may also be administered in the form of suppositories for rectal or vaginal administration of the drug. These compositions can be prepared by mixing the drug with a suitable non-irritating excipient which is solid at ordinary temperatures but liquid at the rectal or vaginal temperature and will therefore melt in the rectum or vagina to release the drug. Such materials include cocoa butter and polyethylene glycols.

The pharmaceutical compositions may be in the form of a sterile injectable aqueous or oleaginous suspension. This suspension may be formulated according to the known art using those suitable dispersing or wetting agents and suspending agents which have been mentioned above. The sterile injectable preparation may also be sterile injectable solution or suspension in a non-toxic parentally acceptable diluent or solvent, for example as a solution in 1,3-butanediol. Among the acceptable vehicles and solvents that may be employed are water, Ringer's solution and isotonic sodium chloride solution. In addition, sterile, fixed oils are conventionally employed as a solvent or suspending medium. For this purpose any bland fixed oil may be employed including synthetic mono- or diglycerides. In addition, fatty acids such as oleic acid find use in the preparation of injectables.

Compounds of the invention may also be administered transdermally using methods know to those skilled in the art (see, for example: Chien; "transdermal Controlled Systemic Medications"; Marcel Dekker, Inc.; 1987. Lipp et al. WO 94/04157 3 Mar. 1994).

Compounds of general Formula I may be administered parenterally in a sterile medium. The drug, depending on the vehicle and concentration used, can either be suspended or dissolved in the vehicle. Advantageously, adjuvants such as local anesthetics, preservatives and buffering agents can be dissolved in the vehicle.

For administration to non-human animals, the composition may also be added to the animal feed or drinking water. It will be convenient to formulate these animal feed and drinking water compositions so that the animal takes in an appropriate quantity of the composition along with its diet. It will also be convenient to present the composition as a premix for addition to the feed or drinking water.

For all regimens of use disclosed herein for compounds of formula I, the daily oral dosage regimen will preferably be from 0.01 to 200 mg/Kg of total body weight. The daily dosage for administration by injection, including intravenous, intramuscular, subcutaneous and parenteral injections, and use of infusion techniques will preferably be from 0.01 to 200 mg/Kg of total body weight. The daily rectal dosage regimen will preferably be from 0.01 to 200 mg/Kg of total body weight. The daily vaginal dosage regimen will preferably be from 0.01 to 200 mg/Kg of total body weight. The daily topical dosage regimen will preferably be from 0.01 to 200 mg administered between one to four times daily. The transdermal concentration will preferably be that required to maintain a daily dose of from 0.01 to 200 mg/Kg. The daily inhalation dosage regimen will preferably be from 0.01 to 200 mg/Kg of total body weight.

It will be understood, however, that the specific dose level for any particular patient will depend upon a variety of factors including the activity of the specific compound employed, the age, body weight, general health, sex, diet, time of administration, route of administration, and rate of excretion, drug combination and the severity of the particular disease undergoing therapy.

Preferred compounds of the invention will have certain pharmacological properties. Such properties include, but are not limited to oral bioavailability, low toxicity, low serum protein binding and desirable in vitro and in vivo half-lives.

Assays may be used to predict these desirable pharmacological properties. Assays used to predict bioavailability include transport across human intestinal cell monolayers, including Caco-2 cell monolayers. Toxicity to cultured hepatocycles may be used to predict compound toxicity. Penetration of the blood brain barrier of a compound in humans may be predicted from the brain levels of the compound in laboratory animals given the compound intravenously.

Serum protein binding may be predicted from albumin binding assays. Such assays are described in a review by Oravcová, et al. (Journal of Chromatography B (1996) volume 677, pages 1-27).

Compound half-life is inversely proportional to the frequency of dosage of a compound. In vitro half-lifes of compounds may be predicted from assays of microsomal half-life as described by Kuhnz and Gieschen (Drug Metabolism and Disposition, (1998) volume 26, pages 1120-1127).

Representative illustrations of the preparation of the present invention are given in Scheme I-Scheme VI. Those having skill in the art will recognize that the starting materials may be varied and additional steps may be employed to produce compounds encompassed by the present invention.

Scheme I

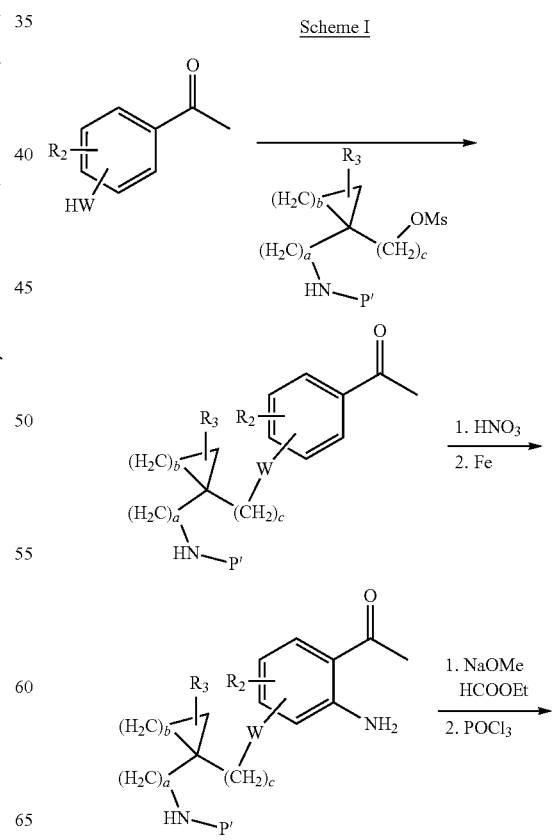

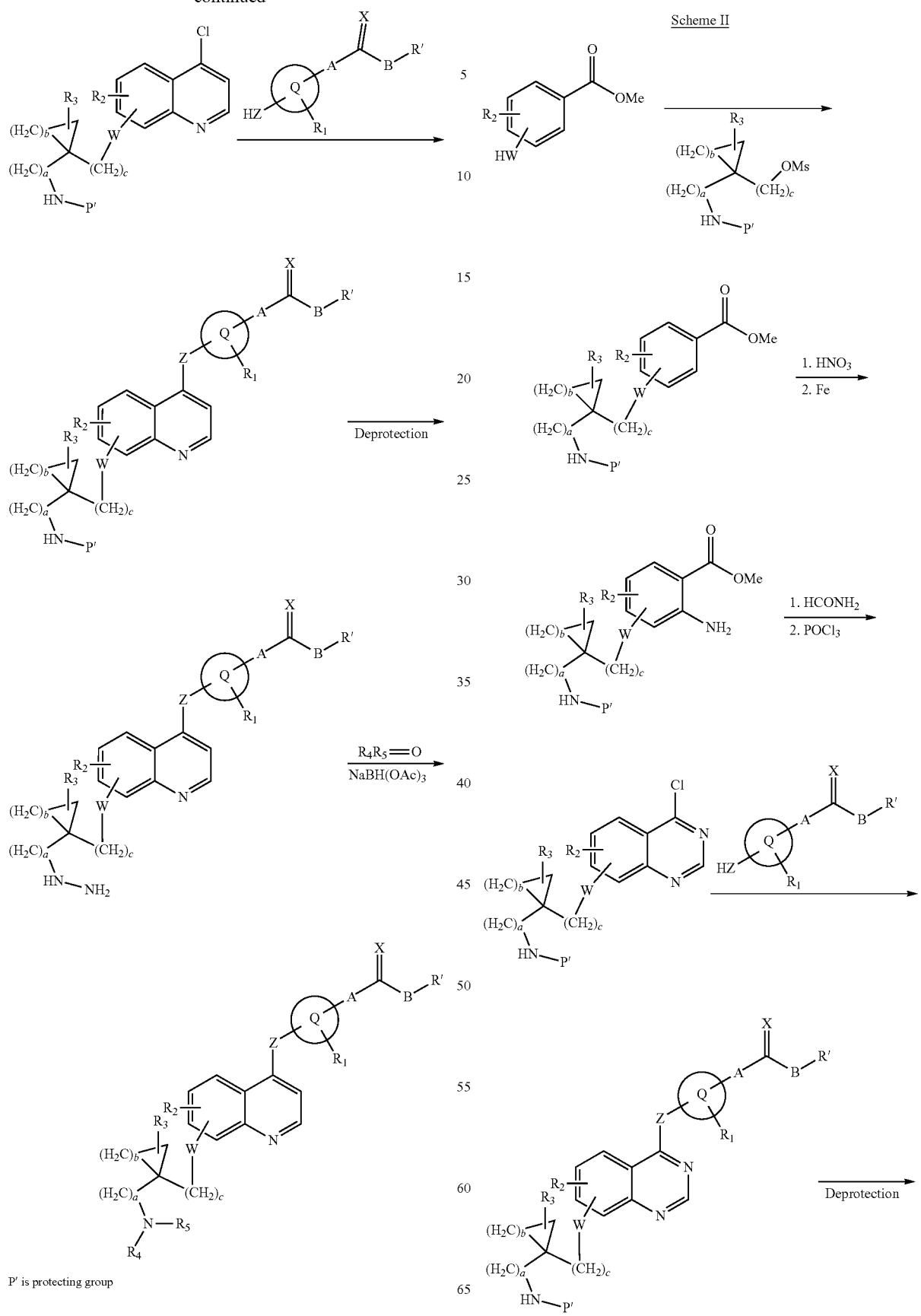

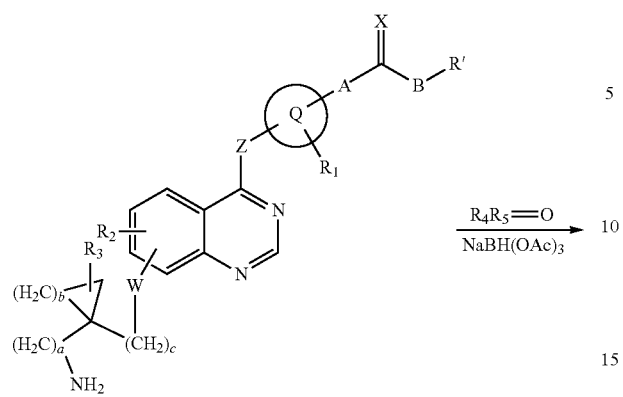
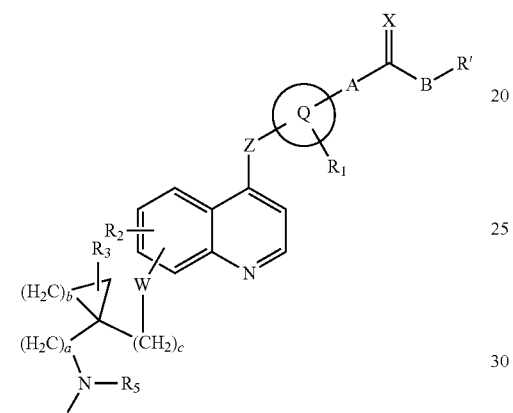
P' is protecting group
Scheme III
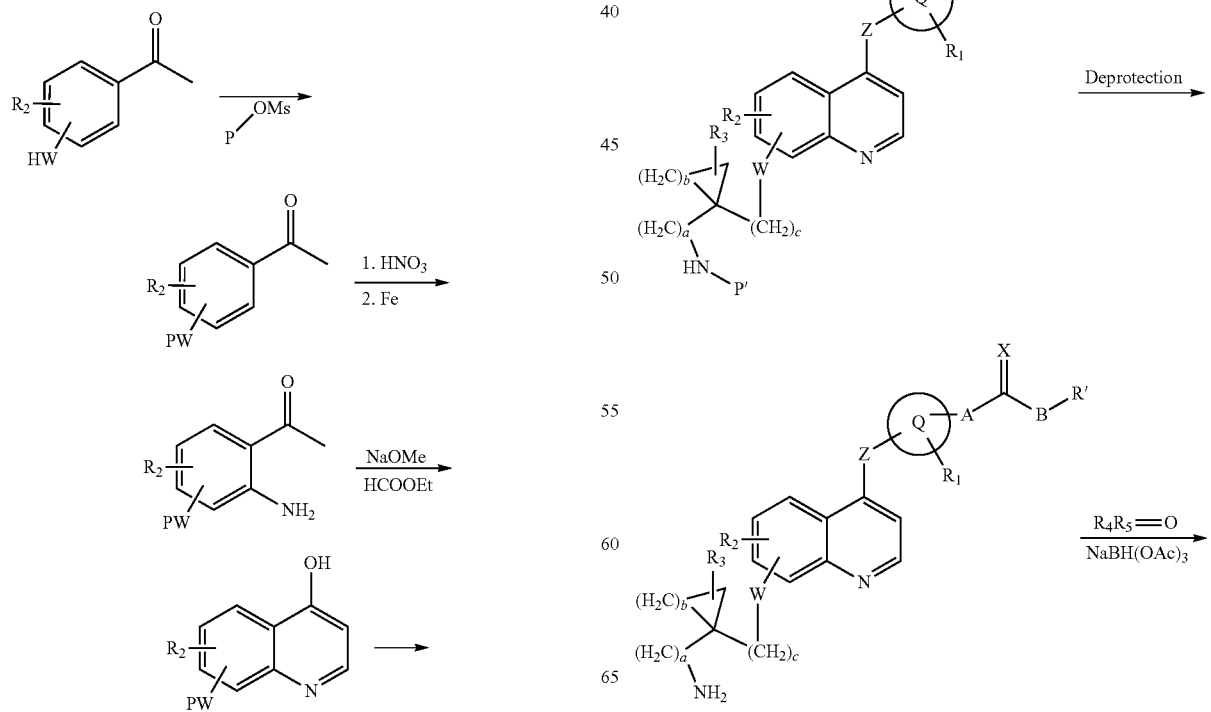

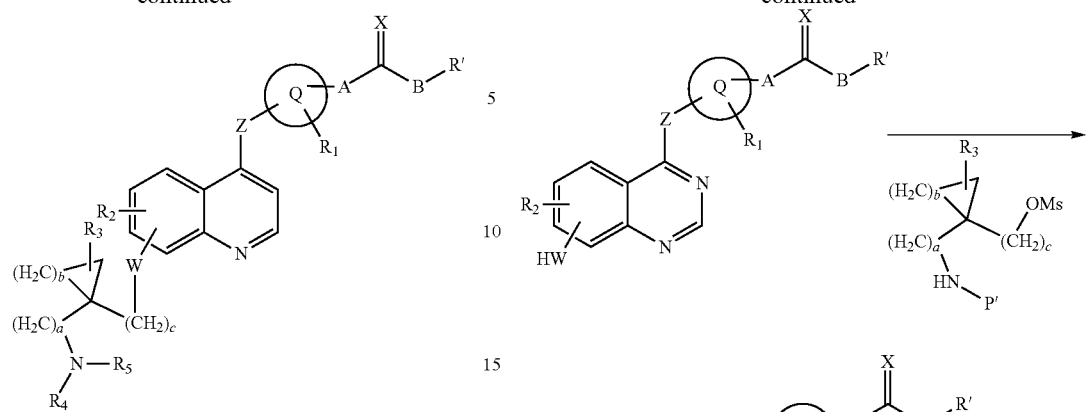
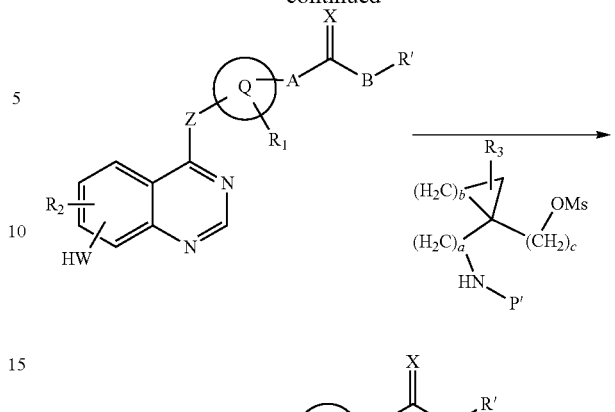
P and P' are independently protecting group
Scheme IV
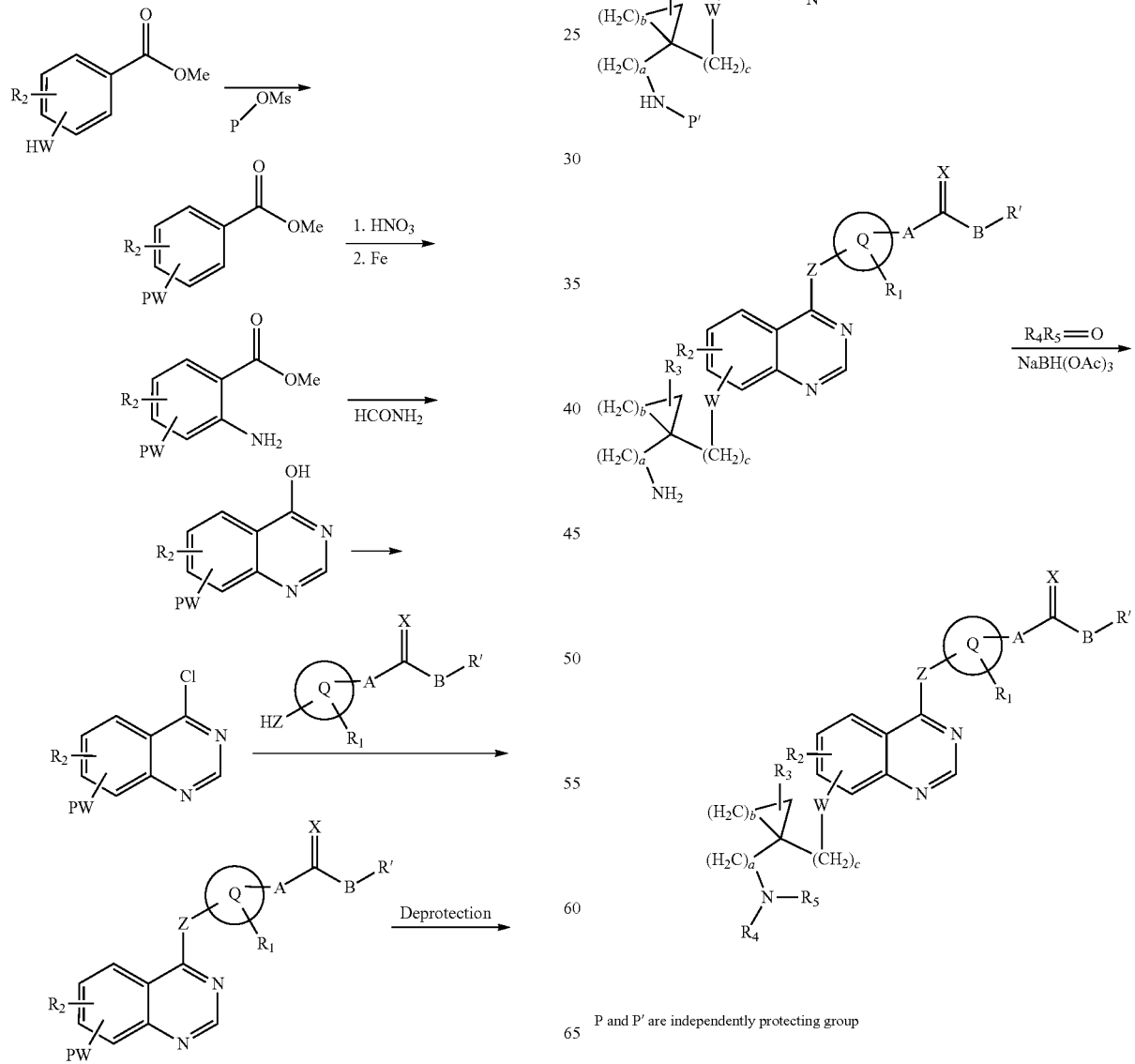
P and P' are independently protecting group Scheme V
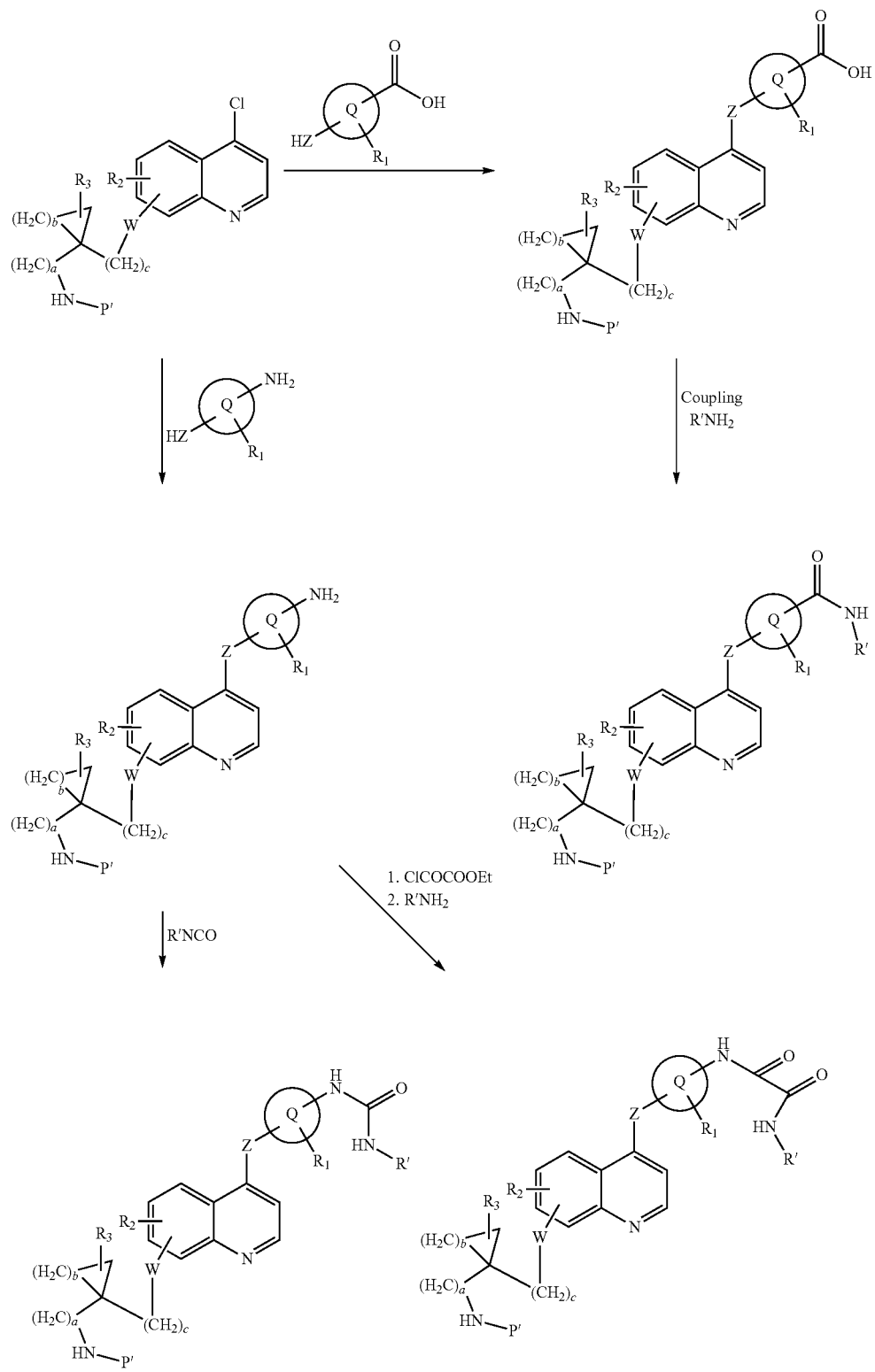
P' is protecting group
All above products can be deprotected to give their corresponding derivatives.

Scheme VI
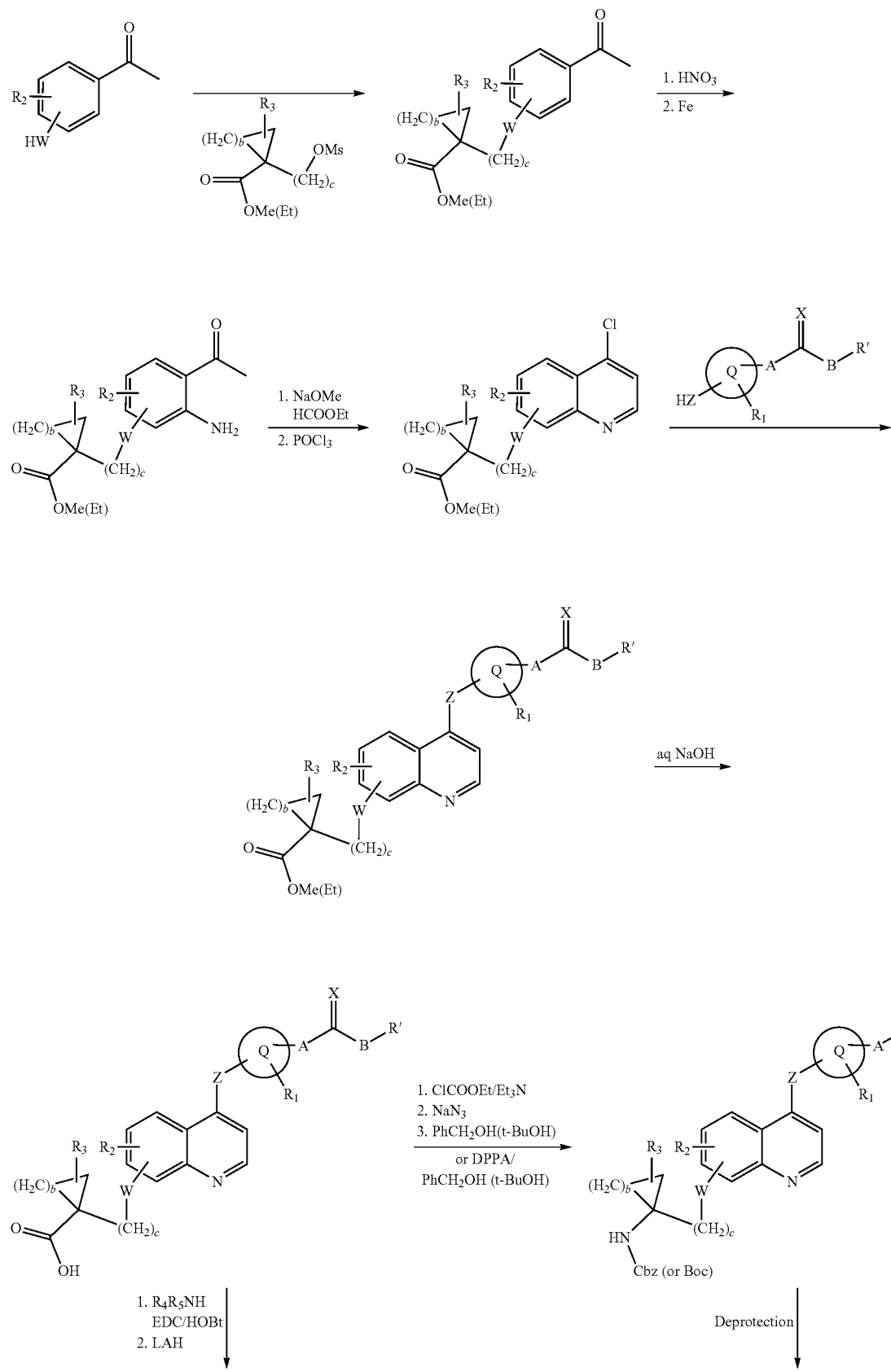

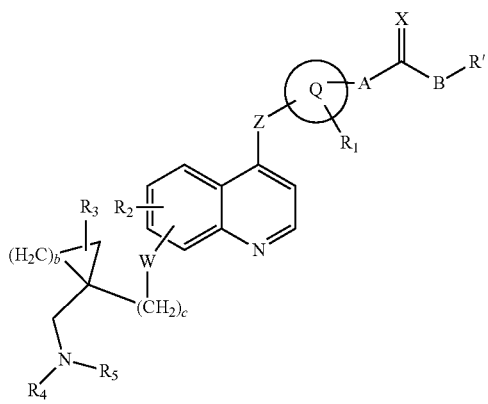
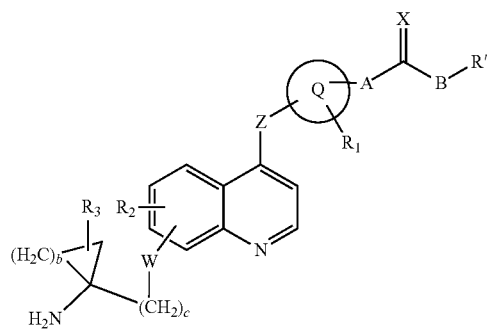

The quinazoline scaffold derivatives can be made similarly according to the chemistry described above.

The following examples of Formula II, but not limited, can be prepared similarly according to the methods described in Scheme I-Scheme VI.

Formula II

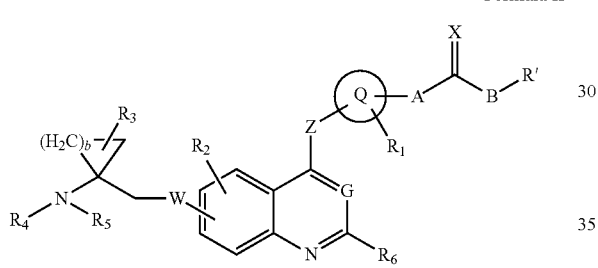

Wherein
A is selected from direct bond or —N(R')—;
B is selected from direct bond, —N(R')—, —C(=X)— or —C(=X)N(R')—;
X is selected from O or S;
R' is selected from H, halogen, halogeno-lower alkyl, lower alkyl, aryl or heterocyclyl;
W and Z are each independently selected from O, or N—R;
G is selected from C—R, or N;
$R_1$, $R_2$ and $R_3$ are each independently selected from H, halogen, halogeno-lower alkyl, lower alkyl, hydroxy, lower alkoxy;
$R_4$ and $R_5$ are each independently selected from H, halogen, halogeno-lower alkyl, lower alkyl, hydroxy, lower alkoxy, lower alkoxyalkoxy, lower alkenyl, lower alkynyl, lower alkyl-OC(=O)—, ary-OC(=O)—, ary lower alkylenyl-OC(=O)—, lower alkyl-C(=O)—, ary-C(=O)— or ary lower alkylenyl-C(=O)—;
$R_6$ is H or F;
b is selected from 1, 2 or 3;
ring Q is selected from following groups:

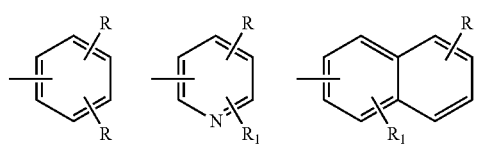
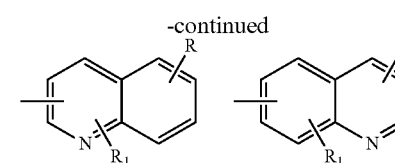
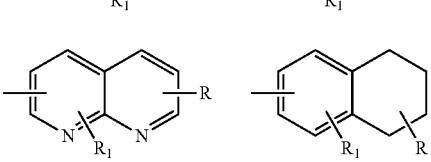
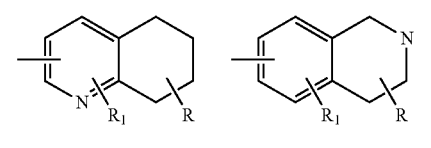
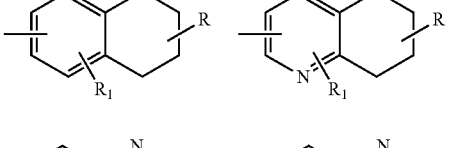
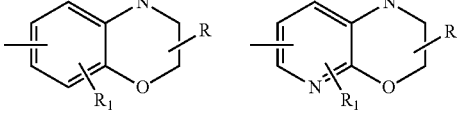

or a pharmaceutically acceptable salt thereof.

The following examples of Formula III, but not limited, can also be prepared similarly according to the methods described in Scheme I-Scheme VI.

Formula III

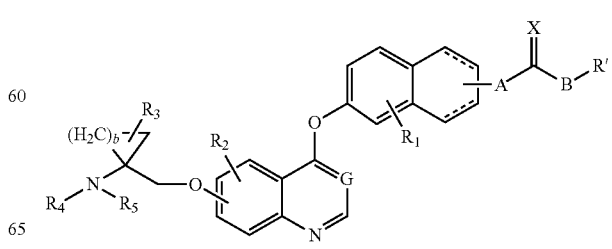

Wherein

A is selected from direct bond or —N(R')—;

B is selected from —N(R')—, —C(=X)— or —C(=X)N(R')—;

R' is selected from H, halogen, halogeno-lower alkyl, lower alkyl, aryl or heterocyclyl;

X is selected from O or S

G is selected from C—R, or N;

$R_1$, $R_2$ and $R_3$ are each independently selected from H, halogen, halogeno-lower alkyl, lower alkyl, hydroxy, lower alkoxy;

$R_4$ and $R_5$ are each independently selected from H, halogen, halogeno-lower alkyl, lower alkyl, hydroxy, lower alkoxy, lower alkoxyalkoxy, lower alkenyl, lower alkynyl, lower alkyl-OC(=O)—, ary-OC(=O)—, ary lower alkylenyl-OC(=O)—, lower alkyl-C(=O)—, ary-C(=O)— or ary lower alkylenyl-C(=O)—;

b is selected from 1, 2 or 3;

or a pharmaceutically acceptable salt thereof.

The following examples of Formula IV, but not limited, can also be prepared similarly according to the methods described in Scheme I-Scheme V.

Formula IV

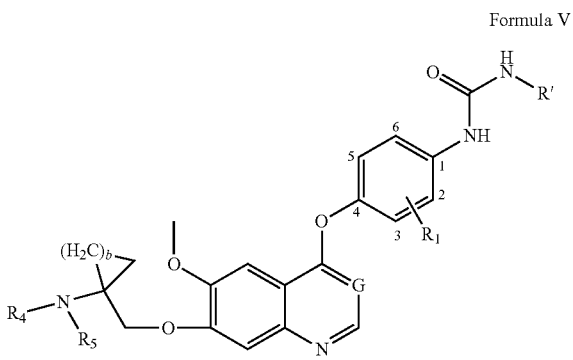

Wherein $R_1$ is selected from H or 5-F;

$R_4$ is H or $CH_3$;

$R_5$ is selected from H, $CH_3$, $CH_3CO$—, BzlOCO— or t-BuOCO—;

G is CH or N;

R' is selected from the following groups: H, $CH_3$,

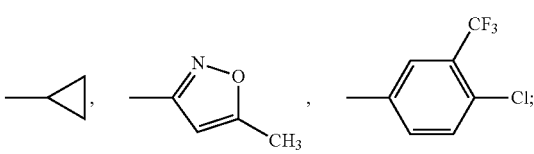

or a pharmaceutically acceptable salt thereof.

The following examples of Formula V, but not limited, can also be prepared similarly according to the methods described in Scheme I-Scheme VI.

Formula V

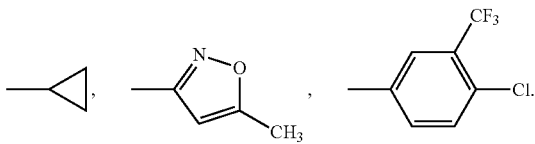

Wherein $R_1$ is selected from H, 3-F or 2-Cl;

$R_4$ is H or $CH_3$;

$R_5$ is selected from H, $CH_3$, $CH_3CO$—, BzlOCO— or t-BuOCO—;

G is CH or N;

R' is selected from the following groups: $CH_3$,

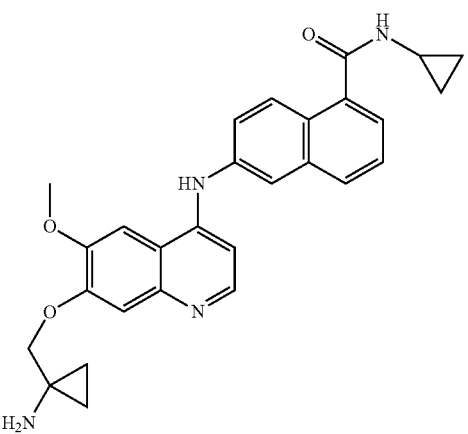

or a pharmaceutically acceptable salt thereof.

The following examples, but not limited, can also be prepared similarly according to the methods described in Scheme I-Scheme VI.

25
-continued
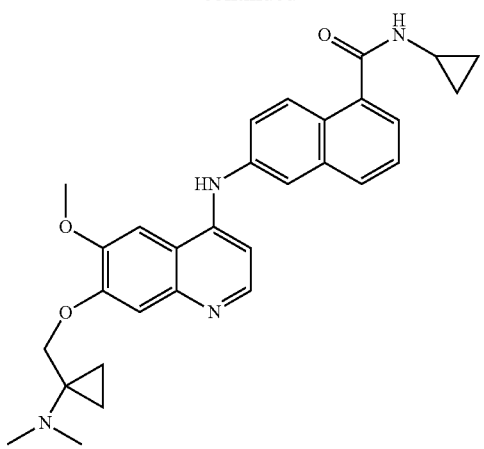
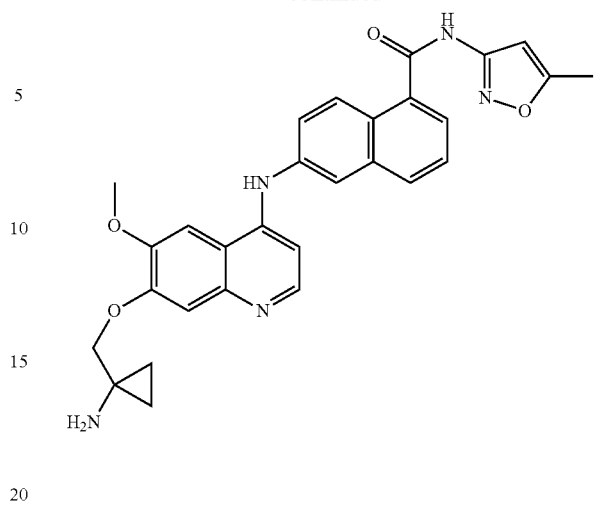
26
-continued
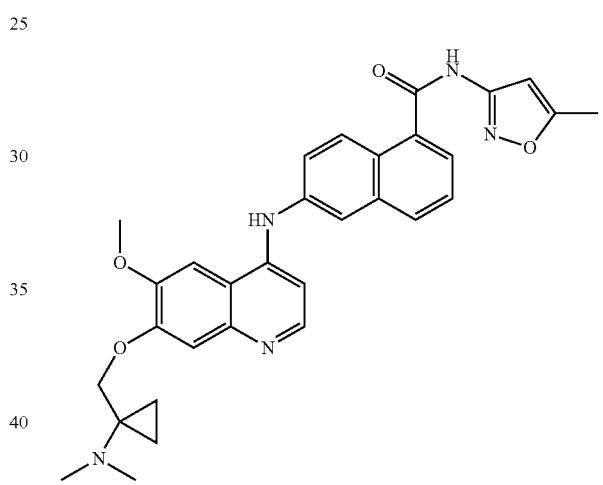
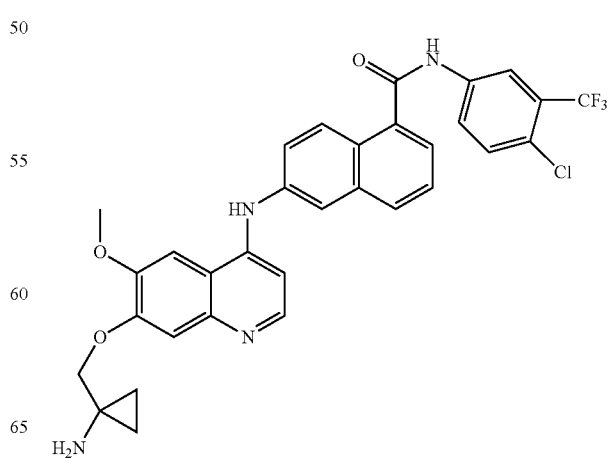

-continued
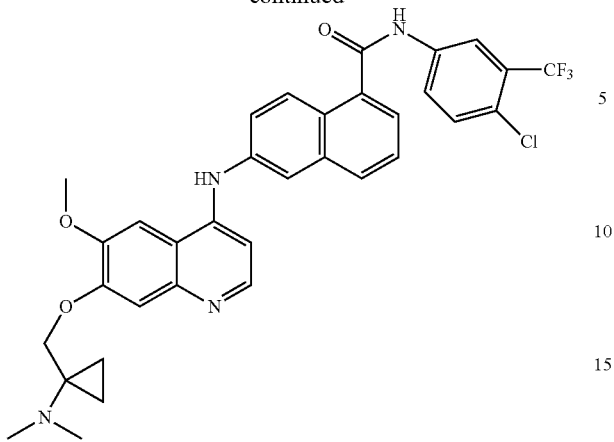
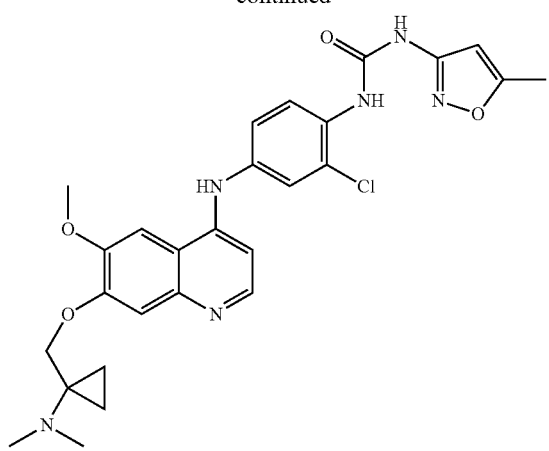
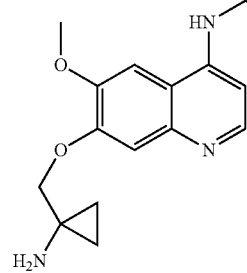
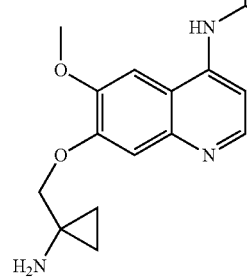
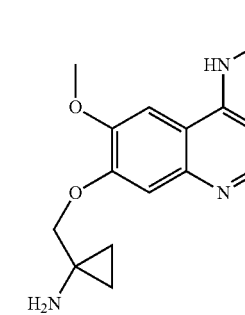

29
-continued
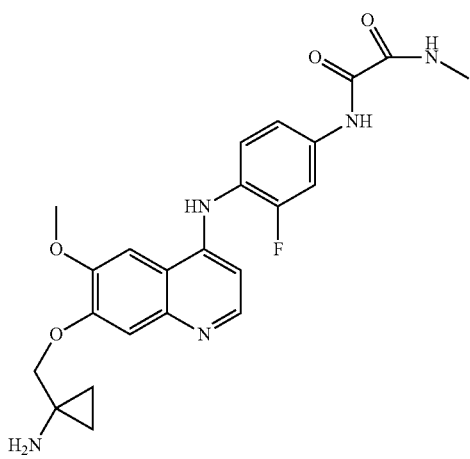
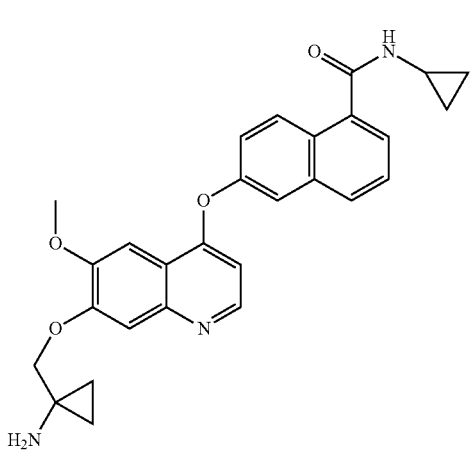
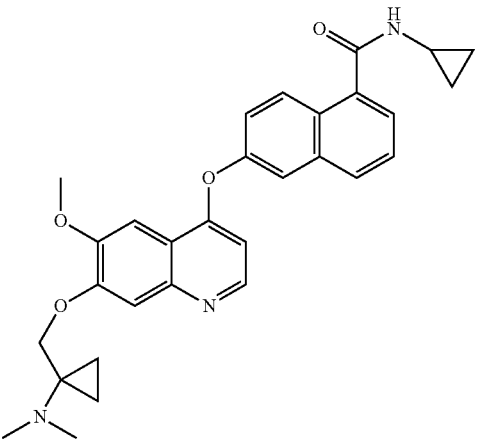
30
-continued
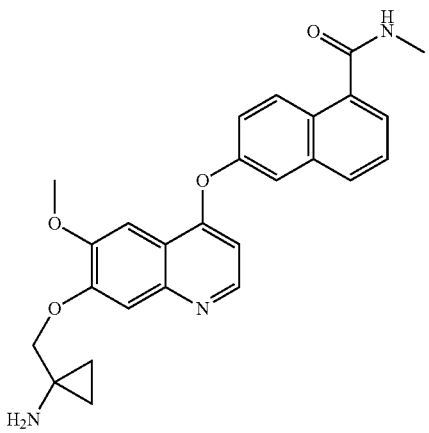
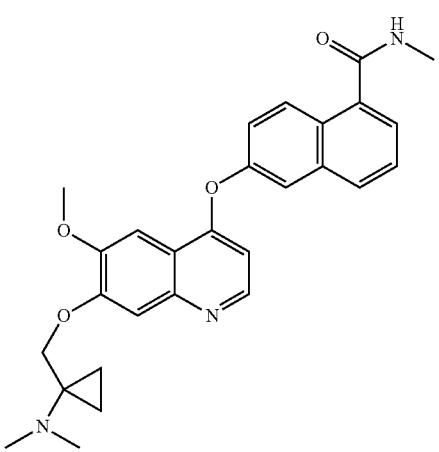
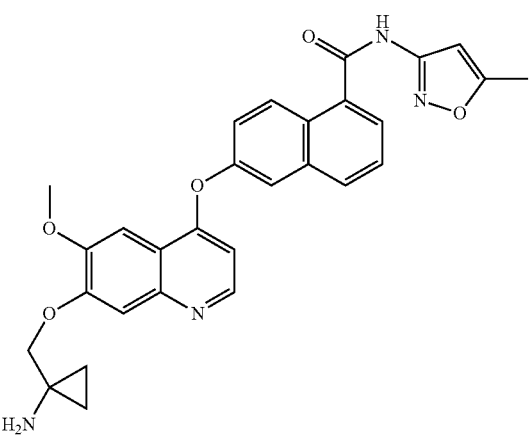

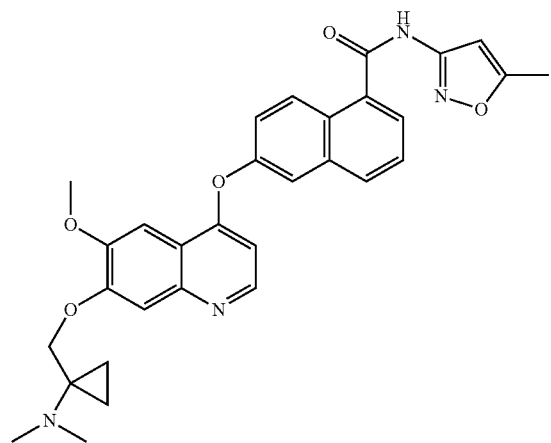
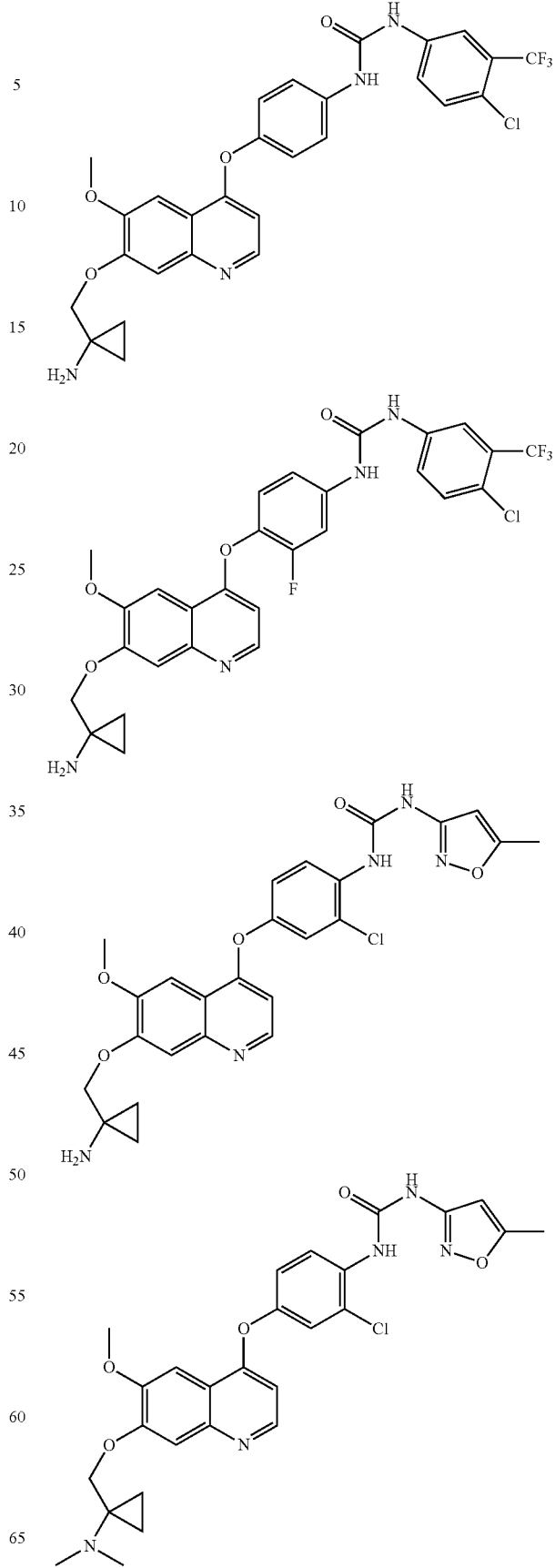

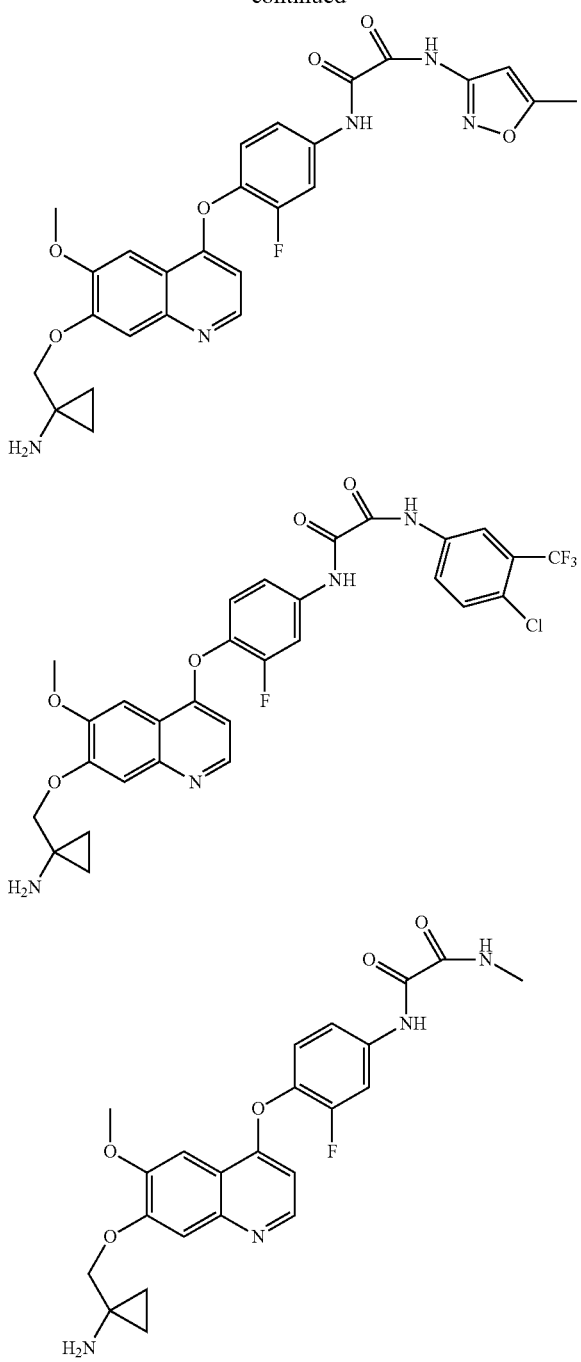

or a pharmaceutically acceptable salt thereof.

In some cases protection of certain reactive functionalities may be necessary to achieve some of above transformations. In general the need for such protecting groups will be apparent to those skilled in the art of organic synthesis as well as the conditions necessary to attach and remove such groups. Those skilled in the art will recognize that in certain instances it will be necessary to utilize different solvents or reagents to achieve some of the above transformations.

The disclosures in this application of all articles and references, including patents, are incorporated herein by reference in their entirety.

The invention is illustrated further by the following examples, which are not to be construed as limiting the invention in scope or spirit to the specific procedures described in them.

The starting materials are and various intermediates may be obtained from commercial sources, prepared from commercially available organic compounds, or prepared using well known synthetic methods.

Representative methods for preparing intermediates of the invention are set forth below in the examples.

The following abbreviations have been used and others are all standard chemical formula representation.

EtOH: ethanol, MeOH: methanol, RT: room temperature, DMA: N,N-dimethylacetamide, DIPEA: diisopropylethylamine, DCM: Dichloromethane, DMF: N,N-dimethylformamide, DMAP: dimethylaminopyridine, EtOAc: ethyl acetate, HOBt: 1-hydroxybenzotriazole hydrate, EDC: 1-(3-dimethylaminopropyl)-3-ethylcarbodiimide hydrochloride, MsCl: Methanesulfonyl chloride, eq: equivalent, g: gram, mg: milligram, ml: milliliter, μl: microliter Example 1

Benzyl 1-((6-methoxy-4-(5-(methylcarbamoyl)naphthalen-2-yloxy)quinolin-7-yloxy)methyl)cyclopropylcarbamate Method A:

6-Hydroxy-1-naphthoic acid (1 g) was mixed with acetic anhydride (5 ml) and sulfuric acid (5 drops). The mixture was refluxed for 3 hours and cooled at RT for 10 hours then mixed with water (15 ml). The solid was filtered and washed with water and cold MeOH to give the product as 6-acetoxy-1-naphthoic acid (900 mg) that was mixed with EDC (1.5 eq), HOBt (1 eq), MeNH$_2$—HCl (2.5 eq, methylamine hydrochloride) and DIPEA (2.5 eq) in DCM (25 ml). The reaction was stirred at RT overnight and washed with NaHCO$_3$ solution, dried. The solution was evaporated and mixed with 15% KOH (2 ml) in MeOH (10 ml) further stirred at RT for 30 minutes. The solvent was evaporated and the residue was adjusted to weak acidic with 2N HCl, the solid was filtered and washed with water twice and cold MeOH to give 6-Hydroxy-N-methyl-1-naphthamide (720 mg).

7-Benzyloxy-6-methoxy-quinolin-4-ol (WO2006108059) (1 g) was refluxed with POCl$_3$ (8 ml) for 3 hours. The reaction was evaporated and dissolved into DCM (80 ml) that was washed with ice water followed by brine. The organic layer was dried with Na$_2$SO$_4$ and evaporated to dryness to give a dark yellow solid as 4-chloro-7-benzyloxy-6-methoxy-quinoline that was mixed with 6-Hydroxy-N-methyl-1-naphthamide (600 mg), DMAP (1.5 eq) in dioxane (40 ml). The reaction was refluxed for three days and diluted with EtOAc, water and extracted with EtOAc three times. The combined organic layer was washed with water, brine and dried. The solution was evaporated and purified with silica gel column to give 6-(7-(benzyloxy)-6-methoxyquinolin-4-yloxy)-N-methyl-1-naphthamide (210 mg). This product was mixed with Pd/C (120 mg, 10%), HCONH$_4$ (210 mg) in EtOH (20 ml). The mixture was refluxed for 1 hour and evaporated then mixed with water (2 ml). The solid was filtered and washed with water twice and cold MeOH as 6-(7-hydroxy-6-methoxyquinolin-4-yloxy)-N-methyl-1-naphthamide for next step without further purification.

N—CBZ-amino-1-(hydroxymethyl)cyclopropane (similarly prepared according to JMC 31, 2004, 1998) (250 mg) was dissolved into DCM (25 ml) with DIPEA (250 l) and stirred at 0° C. for 15 minutes. To the reaction was added MsCl (1.1 eq) and stirred for 30 minutes. The reaction was washed with NaHCO$_3$ solution, water, brine and dried with Na$_2$SO$_4$. The solution was evaporated to give N—CBZ-amino-1-(methylsulfonyloxymethyl)cyclopropane as an off white solid. This solid was mixed with above 6-(7-hydroxy-6-methoxyquinolin-4-yloxy)-N-methyl-1-naphthamide and Cs$_2$CO$_3$ (250 mg) in DMA (4 ml). The reaction was heated at 100° C. for 10 hours and mixed with EtOAc and water, then filtered, further extracted with EtOAc. The combined organic layer was evaporated and purified with silica gel column to give the titled product. Mass: (M+1), 578

Method B:

4-Chloro-7-benzyloxy-6-methoxy-quinoline (3 g) was mixed with 6-Hydroxy-1-naphthoic acid (2 g) and KOH (2.5 g) in DMSO (11 ml). The mixture was heated at 130° C. for 5 hours and cooled to RT. The reaction was then poured into a stirred water (60 ml) solution slowly to give a precipitate that was filtered to give 6-(7-(benzyloxy)-6-methoxyquinolin-4-yloxy)-1-naphthoic acid (2.8 g). This product was mixed with MeNH$_2$—HCl (2 g), EDC (3.3 g), HOBt (2 g) and DIPEA (4 ml) in DCM (80 ml). The reaction was stirred at RT overnight and washed with NaHCO$_3$ solution, dried. The solution was evaporated and purified with silica gel column to give 6-(7-(benzyloxy)-6-methoxyquinolin-4-yloxy)-N-methyl-1-naphthamide. The title compound then was prepared according to the same procedures described in Method A.

Method C:

Dimethyl 1,1-cyclopropanedicarboxylate (5 ml) was mixed with NaOH (1.4 g) in MeOH (40 ml)/water (4 ml). The reaction mixture was stirred at RT overnight and the solvent was evaporated. To the residue was added ether (50 ml), water (50 ml) and extracted once. The aqueous layer was acidified with 6N HCl and extracted three times with ether, the combined organic layer was washed with brine, dried and evaporated to give 1-(methoxycarbonyl)cyclopropanecarboxylic acid (4 g).

The above product was mixed with DIPEA (1.2 eq) in THF and stirred at 0° C. for 10 minutes, to the reaction was added ethyl chloroformate (1 eq) slowly and further stirred for 1.5 hours from 0° C. to RT. To the reaction cooled at 0° C. was added NaBH$_4$ (1.5 eq) slowly followed by MeOH (2 eq) and stirred for 2 hours from 0° C. to RT. The reaction was diluted with EtOAc, water and extracted with EtOAc three times. The combined organic layer was washed with water, brine and dried. The solution was evaporated and purified with silica gel column to give methyl 1-(hydroxymethyl)cyclopropanecarboxylate (2.5 g).

The above product was dissolved into DCM (40 ml) with DIPEA (4 ml) and stirred at 0° C. for 15 minutes. To the reaction was added MsCl (1.1 eq) and stirred for 30 minutes. The reaction was washed with NaHCO$_3$ solution, water, brine and dried with Na$_2$SO$_4$. The solution was evaporated and mixed with 4-hydroxy-3-methoxy-acetophenone (0.9 eq) and K$_2$CO$_3$ (1.5 eq) in DMF (20 ml). The reaction was heated at 100° C. for 6 hours and diluted with EtOAc, water and extracted with EtOAc three times. The combined organic layer was washed with water, brine and dried further evaporated to give methyl 1-((4-acetyl-2-methoxyphenoxy)methyl)cyclopropane-carboxylate (1.8 g). This product was dissolved into acetic acid (5 ml) and stirred at RT, to the reaction was very slowly added nitric acid (8 ml, 60%) and stirred at RT for 1 hour. The reaction was poured into ice-water and extracted with EtOAc three times. The combined organic layer was washed with water, brine and dried.

The solution was evaporated and mixed with iron powder (1.5 g) and NH$_4$Cl (150 mg) in EtOH/H$_2$O (80 ml, 9/1). The reaction was refluxed for 3 hours and filtered through Celite followed by evaporation. The residue was mixed with EtOAc/H$_2$O and extracted with EtOAc three times. The combined organic layer was washed with water, brine and dried. The solution was evaporated and purified with silica gel column to give methyl 1-((5-amino-4-acetyl-2-methoxyphenoxy)methyl)-cyclopropanecarboxylate (1 g).

The above product was mixed with fresh prepared NaOMe (2 eq) in ethylene glycol dimethyl ether (30 ml) and stirred at RT for 1 hour. To the mixture was added HCOOEt (3 eq), the reaction was stirred at RT overnight and neutralized with 6N HCl. The reaction was evaporated with silica gel to dryness and purified on silica gel column with DCM/MeOH as eluent to give methyl 1-((4-hydroxy-6-methoxyquinolin-7-yloxy)methyl)cyclopropanecarboxylate (600 mg). This product was refluxed with POCl$_3$ (4 ml) for 3 hours and evaporated, then dissolved into DCM. The solution was washed with ice water followed by brine. The organic layer was dried with Na$_2$SO$_4$ and evaporated to give methyl 1-((4-chloro-6-methoxyquinolin-7-yloxy)methyl)cyclopropanecarboxylate (500 mg).

The above product was mixed with DMAP (1.5 eq), 6-Hydroxy-N-methyl-1-naphthamide (300 mg) in dioxane (20 ml). The reaction was refluxed for three days and diluted with EtOAc, water and extracted with EtOAc three times. The combined organic layer was washed with water, brine and dried. The solution was evaporated and purified with silica gel column to give methyl 1-((6-methoxy-4-(5-(methylcarbamoyl)naphthalen-2-yloxy)quinolin-7-yloxy)methyl)-cyclopropanecarboxylate (200 mg). This product of was mixed with 15% NaOH (3 eq) in MeOH (15 ml) and refluxed for 30 minutes. The reaction was evaporated and adjusted to PH=6, then diluted with EtOAc, water and extracted with EtOAc three times. The combined organic layer was washed with water, brine, dried and evaporated to give 1-((6-methoxy-4-(5-(methylcarbamoyl)naphthalen-2-yloxy)quinolin-7-yloxy)methyl)cyclopropanecarboxylic acid (120 mg).

The above product was mixed with DIPEA (0.3 ml) in acetone (5 ml) at 0° C. To the reaction was slowly added ClCOOCH$_2$CH(CH$_3$)$_2$ (100 l) and stirred for 2 hours from 0° C. to RT. NaN$_3$ (0.2 g)/H2O (0.5 ml) was added to the reaction and stirred for 30 minutes. The reaction was diluted with EtOAc, water and extracted with EtOAc three times. The combined organic layer was washed with water, brine, dried and evaporated without further purification. The residue was mixed with benzyl alcohol (150 l) in toluene (10 ml) and refluxed for 1.5 hour. The reaction was evaporated and purified with silica gel column to give the titled product. Mass: (M+1), 578

Example 2

Benzyl 1-((4-(5-(cyclopropylcarbamoyl)naphthalen-2-yloxy)-6-methoxyquinolin-7-yloxy)methyl)-cyclopropylcarbamate The title compound was prepared by similar manner to Example 1, by using cyclopropylamine instead of methylamine hydrochloride. Mass: (M+1), 604

Example 3

6-(7-((1-Aminocyclopropyl)methoxy)-6-methoxyquinolin-4-yloxy)-N-methyl-1-naphthamide The product of Example 1 (100 mg) was mixed with Pd/C (10%, 40 mg) in EtOH (30 ml) and hydrogenated at 50 psi for 12 hours. The reaction was filtered through Celite and evaporated to give the titled product. Mass: (M+1), 444

The product of Example 1 (100 mg) was mixed with acetic acid (1 ml) and 33% HBr/acetic acid (0.6 ml). The reaction was stirred at RT for 1 hour and diluted with EtOAc/H₂O then basified with Na₂CO₃. The organic layer was dried, evaporated and purified with silica gel column to give the titled product. Mass: (M+1), 444

Example 4

6-(7-((1-(Dimethylamino)cyclopropyl)methoxy)-6-methoxyquinolin-4-yloxy)-N-methyl-1-naphthamide The product of Example 3 (60 mg) was mixed with HCHO (30 l, 37% in H₂O), NaBH(OAc)₃ (2 eq) in DCM (5 ml) and stirred at RT for 3 hours. The reaction was evaporated and purified with silica gel column to give the titled product. Mass: (M+1), 472

Example 5

6-(7-((1-Aminocyclopropyl)methoxy)-6-methoxyquinolin-4-yloxy)-N-cyclopropyl-1-naphthamide The title compound was prepared by similar manner to Example 3, starting from the compound of Example 2. Mass: (M+1), 470

Example 6

N-cyclopropyl-6-(7-((1-(dimethylamino)cyclopropyl)methoxy)-6-methoxyquinolin-4-yloxy)-1-naphthamide The title compound was prepared by similar manner to Example 4, starting from the compound of Example 5. Mass: (M+1), 498

Example 7

6-(7-((1-Aminocyclopropyl)methoxy)-6-methoxyquinolin-4-yloxy)-N-(5-methylisoxazol-3-yl)-1-naphthamide 6-Acetoxy-1-naphthoic acid (200 mg, from Example 1) was mixed with DIPEA (1.2 eq) in THF and stirred at 0° C. for 10 minutes, to the reaction was added ethyl chloroformate (1 eq) slowly and further stirred for 1.5 hours from 0° C. to RT. To the reaction was added DIPEA (1.2 eq) and 3-amino-5-methylisoxazole (1.2 eq), the reaction was stirred at RT for 12 hours and mixed with EtOAc/H₂O, further extracted with EtOAc and dried. The solution was evaporated and mixed with 15% KOH (2 ml) in MeOH (10 ml) further stirred at RT for 30 minutes. The solvent was evaporated and the residue was adjusted to weak acidic with 2N HCl, the solid was filtered and washed with water twice and cold MeOH to give 6-Hydroxy-N-(5-methylisoxazol-3-yl)-1-naphthamide (90 mg).

The title compound then was prepared by similar manner to Example 1, Example 3 by using 6-Hydroxy-N-(5-methylisoxazol-3-yl)-1-naphthamide. Mass: (M+1), 511

Example 8

6-(7-((1-(Dimethylamino)cyclopropyl)methoxy)-6-methoxyquinolin-4-yloxy)-N-(5-methylisoxazol-3-yl)-1-naphthamide The title compound was prepared by similar manner to Example 4, starting from the compound of Example 7. Mass: (M+1), 539

Example 9

6-(7-((1-Aminocyclopropyl)methoxy)-6-methoxyquinolin-4-yloxy)-N-(3-methylisoxazol-5-yl)-1-naphthamide The title compound was prepared by similar manner to Example 7, by using 5-amino-3-methylisoxazole instead of 3-amino-5-methylisoxazole. Mass: (M+1), 511

Example 10

6-(7-((1-(Dimethylamino)cyclopropyl)methoxy)-6-methoxyquinolin-4-yloxy)-N-(3-methylisoxazol-5-yl)-1-naphthamide The title compound was prepared by similar manner to Example 4, starting from the compound of Example 9. Mass: (M+1), 539

Example 11

6-(7-((1-Aminocyclopropyl)methoxy)-6-methoxyquinolin-4-yloxy)-N-(4-chloro-3-(trifluoromethyl)-phenyl)-1-naphthamide The title compound was prepared by similar manner to Example 7, by using 3-trifluoromethyl-4-chloroaniline instead of 3-amino-5-methylisoxazole. Mass: (M+1), 608

Example 12

N-(4-chloro-3-(trifluoromethyl)phenyl)-6-(7-((1-(dimethylamino)cyclopropyl)methoxy)-6-methoxyquinolin-4-yloxy)-1-naphthamide The title compound was prepared by similar manner to Example 4, starting from the compound of Example 11. Mass: (M+1), 636

Example 13

6-(7-((1-(Cyclopropylmethylamino)cyclopropyl)methoxy)-6-methoxyquinolin-4-yloxy)-N-methyl-1-naphthamide The compound of Example 3 (100 mg) was refluxed with cyclopropanecarbaldehyde (2 eq) in EtOH (8 ml) for 4 hours. To the reaction was added NaBH₄ (2.2 eq), the reaction was refluxed for 20 minutes and evaporated. The residue was purified with silica gel column to give the titled product (40 mg). Mass: (M+1), 498

Example 14

6-(7-((1-(((Cyclopropylmethyl)(methyl)amino)cyclopropyl)methoxy)-6-methoxyquinolin-4-yloxy)-N-methyl-1-naphthamide The compound of Example 13 (40 mg) was mixed with HCHO (2 eq, 37% in $H_2O$), NaBH(OAc)$_3$ (2 eq) in DCM (5 ml) and stirred at RT for 3 hours. The reaction was evaporated and purified with silica gel column to give the titled product (20 mg). Mass: (M+1), 512

Example 15

N-cyclopropyl-6-(7-((1-(cyclopropylmethylamino)cyclopropyl)methoxy)-6-methoxyquinolin-4-yloxy)-1-naphthamide The title compound was prepared by similar manner to Example 13, starting from the compound of Example 5. Mass: (M+1), 524

Example 16

N-cyclopropyl-6-(7-((1-((cyclopropylmethyl)(methyl)amino)cyclopropyl)methoxy)-6-methoxyquinolin-4-yloxy)-1-naphthamide The title compound was prepared by similar manner to Example 14, starting from the compound of Example 15. Mass: (M+1), 538

Example 17

N-(4-chloro-3-(trifluoromethyl)phenyl)-6-(7-((1-(cyclopropylmethylamino)cyclopropyl)methoxy)-6-methoxyquinolin-4-yloxy)-1-naphthamide The title compound was prepared by similar manner to Example 13, starting from the compound of Example 11. Mass: (M+1), 662

Example 18

N-(4-chloro-3-(trifluoromethyl)phenyl)-6-(7-((1-((cyclopropylmethyl)(methyl)amino)cyclopropyl)-methoxy)-6-methoxyquinolin-4-yloxy)-1-naphthamide The title compound was prepared by similar manner to Example 14, starting from the compound of Example 17. Mass: (M+1), 676

Example 19

6-(7-((1-(Cyclopropylmethylamino)cyclopropyl)methoxy)-6-methoxyquinolin-4-yloxy)-N-(5-methylisoxazol-3-yl)-1-naphthamide The title compound was prepared by similar manner to Example 13, starting from the compound of Example 7. Mass: (M+1), 565

Example 20

6-(7-((1-(((Cyclopropylmethyl)(methyl)amino)cyclopropyl) methoxy)-6-methoxyquinolin-4-yloxy)-N-(5-methylisoxazol-3-yl)-1-naphthamide The title compound was prepared by similar manner to Example 14, starting from the compound of Example 19. Mass: (M+1), 579

Example 21

1-(4-(7-((1-Aminocyclopropyl)methoxy)-6-methoxyquinolin-4-yloxy)-3-fluorophenyl)-3-(4-chloro-3-(trifluoromethyl)phenyl)urea Methyl 1-((4-hydroxy-6-methoxyquinolin-7-yloxy)methyl)cyclopropanecarboxylate (600 mg, from Example 1) was mixed with $Cs_2CO_3$ (2 eq) and 1,2-difluoro-4-nitrobenzene (1.2 eq) in acetonitrile/DMF (20 ml, 1/1). The reaction was heated at 60° C. for 1 hour and diluted with EtOAc/$H_2O$ then extracted with EtOAc three times. The combined organic layer was dried, evaporated and purified with silica gel column to give methyl 1-((4-(2-fluoro-4-nitro-phenoxy)-6-methoxyquinolin-7-yloxy)methyl)cyclopropanecarboxylate (300 mg). This product was mixed with iron powder (300 mg) and $NH_4Cl$ (30 mg) in EtOH/$H_2O$ (20 ml, 9/1). The reaction was refluxed for 3 hours and filtered through Celite followed by evaporation. The residue was mixed with EtOAc/$H_2O$ and extracted with EtOAc three times. The combined organic layer was washed with water, brine and dried. The solution was evaporated and purified with silica gel column to give methyl 1-((4-(2-fluoro-4-amino-phenoxy)-6-methoxyquinolin-7-yloxy)methyl)cyclopropanecarboxylate (150 mg).

The above product was mixed with DIPEA (1.5 eq) in DCM (10 ml) and cooled at 0° C. To the reaction was added triphosgene (0.5 eq) and stirred for 1 hour at 0° C. To the reaction was then added DIPEA (1.5 eq) and 3-trifluoromethyl-4-chloroaniline (1.1 eq), further stirred at RT for 4 hours and evaporated. It was purified with silica gel column to give methyl 1-((4-(4-(3-(4-chloro-3-(trifluoromethyl)phenyl)ureido)-2-fluorophenoxy)-6-methoxyquinolin-7-yloxy)methyl) cyclopropanecarboxylate.

The title compound then was prepared by similar manner to Method C in Example 1, starting from the above product. Mass: (M+1), 591

Example 22

1-(4-Chloro-3-(trifluoromethyl)phenyl)-3-(4-(7-((1-(dimethylamino)cyclopropyl)methoxy)-6-methoxyquinolin-4-yloxy)-3-fluorophenyl)urea The compound of Example 21 (40 mg) was mixed with HCHO (2 eq, 37% in $H_2O$), NaBH(OAc)$_3$ (2 eq) in DCM (5 ml) and stirred at RT for 3 hours. The reaction was evaporated and purified with silica gel column to give the titled product (15 mg). Mass: (M+1), 619

Example 23

1-(4-(7-((1-Aminocyclopropyl)methoxy)-6-methoxyquinolin-4-yloxy)-3-fluorophenyl)-3-(5-methylisoxazol-3-yl)urea The title compound was prepared by similar manner to Example 21, by using 3-amino-5-methylisoxazole instead of 3-trifluoromethyl-4-chloroaniline. Mass: (M+1), 494

Example 24

1-(4-(7-((1-(Dimethylamino)cyclopropyl)methoxy)-6-methoxyquinolin-4-yloxy)-3-fluorophenyl)-3-(5-methylisoxazol-3-yl)urea The title compound was prepared by similar manner to Example 22, starting from the compound of Example 23. Mass: (M+1), 522

Example 25

1-(4-(7-((1-Aminocyclopropyl)methoxy)-6-methoxyquinolin-4-yloxy)-2-chlorophenyl)-3-(4-chloro-3-(trifluoromethyl)phenyl)urea The title compound was prepared by similar manner to Example 21, by using 1-fluoro-3-chloro-4-nitrobenzene instead of 1,2-difluoro-4-nitrobenzene. Mass: (M+1), 607

Example 26

1-(4-Chloro-3-(trifluoromethyl)phenyl)-3-(2-chloro-4-(7-((1-(dimethylamino)cyclopropyl)methoxy)-6-methoxyquinolin-4-yloxy)phenyl)urea The title compound was prepared by similar manner to Example 22, starting from the compound of Example 25. Mass: (M+1), 635

Example 27

1-(4-(7-((1-Aminocyclopropyl)methoxy)-6-methoxyquinolin-4-yloxy)-2-chlorophenyl)-3-(5-methylisoxazol-3-yl)urea The title compound was prepared by similar manner to Example 25, by using 3-amino-5-methylisoxazole instead of 3-trifluoromethyl-4-chloroaniline. Mass: (M+1), 510

Example 28

1-(2-Chloro-4-(7-((1-(dimethylamino)cyclopropyl)methoxy)-6-methoxyquinolin-4-yloxy)phenyl)-3-(5-methylisoxazol-3-yl)urea The title compound was prepared by similar manner to Example 22, starting from the compound of Example 27. Mass: (M+1), 538

Examples of Salt Formation:

A compound selected from Example 3-28 (100 mg) was mixed with EtOAc (1 ml) and to the solution was added 2N HCl/Ether solution (0.5 ml). The solution was evaporated to give a off white solid as its HCl salt.

The other pharmaceutical acceptable salts, such as hydrobromic, sulphuric, nitric, phosphoric acid; or succinic, maleic, acetic, fumaric, citic, tartaric, benzoic, p-toluenesulfonic, methanesulfonic, naphthalenesulfonic acid salt can be prepared in the similar manner. It can be made at higher temperatures with EtOH, MeOH or isopropanol as well as with other pharmaceutical acceptable solvents.

Examples of Formulation

The following are the examples of the formulations and these are purely illustrative and in no way to be interpreted as restrictive.

Formulation Example 1

Each capsule contains:

| | |
|---|---:|
| Compound Example 21 (or example 24, or example 25, or example 27, or example 28) | 100.0 mg |
| Corn starch | 23.0 mg |
| Calcium carboxymethyl cellulose | 22.5 mg |
| Hydroxypropylmethyl cellulose | 3.0 mg |
| Magnesium stearate | 1.5 mg |
| | 150.0 mg |

Formulation Example 2

A solution contains:

| | |
|---|---:|
| Compound Example 20 (or example 24, or example 25, or example 27, or example 28) | 1 to 10 g |
| Acetic acid or sodium hydroxide | 0.5 to 1 g |
| Ethyl p-hydroxybenzoate | 0.1 g |
| Purified water | 88.9 to 98.4 g |
| | 100.0 g |

Formulation Example 3

A powder for admixing with feedstuff contains:

| | |
|---|---:|
| Compound Example 20 (or example 24, or example 25, or example 27, or example 28) | 1 to 10 g |
| Corn starch | 98.5 to 89.5 g |
| Light anhydrous silicic acid | 0.5 g |
| | 100.0 g |

What is claimed is:

1. A method of treating cancer in a subject, said method comprising administering an effective amount of a compound of formula I to a patient in need of such treatment

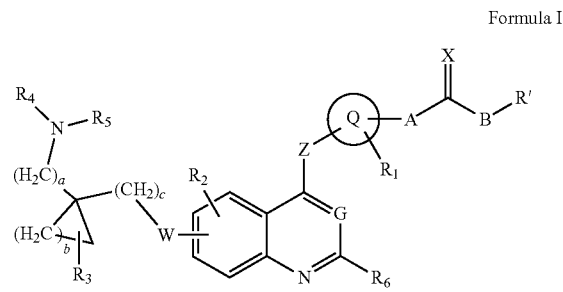

Formula I wherein
R is

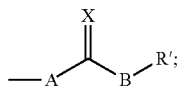

A is selected from direct bond or —N(R')—;
B is selected from direct bond, O, —N(R')—, —C(=X)—
   —C(=X)N(R')—, lower alkylenyl-C(=X)— or lower
   alkylenyl-C(=X)N(R')—;
X is selected from O or S;
R' is selected from H, halogen, halogeno-lower alkyl, lower
   alkyl, hydroxy, lower alkoxy, lower alkoxyalkoxy, lower
   alkenyl, lower alkynyl, amino, alkylamino,
   alkoxyamino, cycloalkyl, cycloalkenyl, aryl, lower aryl,
   heterocyclyl or lower heterocyclyl;
$R_1$, $R_2$ and $R_3$ are each independently selected from H,
   halogen, halogeno-lower alkyl, lower alkyl, hydroxy,
   lower alkoxy, lower alkoxyalkoxy, lower alkenyl, or
   lower alkynyl;
$R_4$ and $R_5$ are each independently selected from H, halogen, halogeno-lower alkyl, lower alkyl, hydroxy, lower alkoxy, lower alkoxyalkoxy, lower alkenyl, lower alkynyl, lower alkyl-OC(=O)—, aryl-OC(=O)—, aryl lower alkylenyl-OC(=O)—, lower alkyl-C(=O)—, aryl-C(=O)—, aryl lower alkylenyl-C(=O)—, lower alkyl-SO$_2$—, ary-SO$_2$—, aryl lower alkylenyl-SO$_2$—, lower alkyl-C(=O)—, aryl-C(=O)—, aryl lower alkylenyl-C(=O)—, lower alkyl-N(R)C(=O)—, aryl-N(R)C(=O)—, or ary lower alkylenyl-N(R)C(=O)—; $R_4$ and $R_5$ connect together to form a 3-8 membered saturated or unsaturated ring with their attached nitrogen;
$R_6$ is selected from H, halogen, halogeno-lower alkyl, lower alkyl;
W and Z are each independently selected from O, S, N—R or CH—R;
G is selected from C—R, C—(CN) or N;
a and c are each independently selected from 0, 1, 2, 3 or 4;
b is selected from 1, 2, 3, 4 or 5; and
   ring Q is selected from following groups:

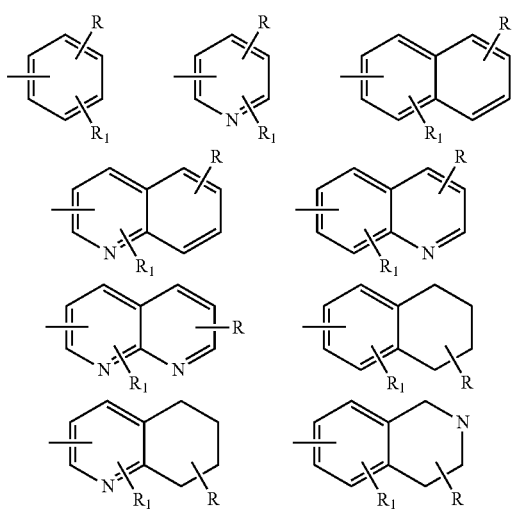

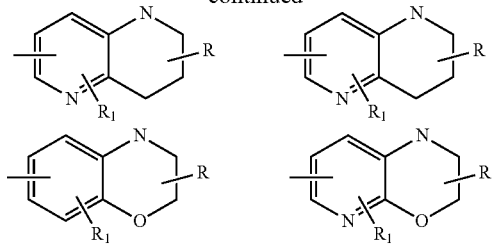

or a pharmaceutically acceptable salt thereof.
2. The method according to claim 1, comprising administering an effective amount of a compound of formula I, wherein
R is

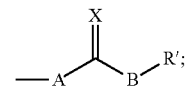

A is selected from direct bond or —N(R')—;
B is selected from direct bond, O, —N(R')—, —C(=X)—
   —C(=X)N(R)—, lower alkylenyl-C(=X)— or lower
   alkylenyl-C(=X)N(R')—;
X is selected from O or S;
R' is selected from H, halogen, halogeno-lower alkyl, lower
   alkyl, hydroxy, lower alkoxy, lower alkoxyalkoxy, lower
   alkenyl, lower alkynyl, amino, alkylamino,
   alkoxyamino, cycloalkyl, cycloalkenyl, aryl, lower aryl,
   heterocyclyl or lower heterocyclyl;
$R_1$, $R_2$, $R_3$, are each independently selected from H, halogen, halogeno-lower alkyl, lower alkyl, hydroxy, lower alkoxy, lower alkoxyalkoxy, lower alkenyl, or lower alkynyl;
$R_4$, and $R_5$ are each independently selected from H, halogen, halogeno-lower alkyl, lower alkyl, lower alkoxy, t-butyl-OC(=O)—, benzyl-OC(=O)— or CH$_3$C(=O)—; $R_4$ and $R_5$ connect together to form a 3-8 membered saturated or unsaturated ring with their attached nitrogen;
$R_6$ is selected from H, halogen, halogeno-lower alkyl, lower alkyl;
W and Z are each independently selected from O, S, N—R or CH—R;
G is selected from C—R, C—(CN) or N;
a and c are each independently selected from 0, 1, 2, 3 or 4;
b is selected from 1, 2, 3, 4 or 5;
ring Q is defined in claim 1;
or a pharmaceutically acceptable salt thereof.
3. The method according to claim 1, comprising administering an effective amount of a compound of formula I, wherein
R is

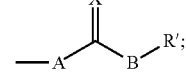

A is selected from direct bond or —N(R')—;
B is selected from direct bond, O, —N(R')—, —C(=X)—
   —C(=X)N(R')—, lower alkylenyl C(=X)— or lower
   alkylenyl-C(=X)N(R')—;

X is selected from O or S;

R' is selected from H, halogen, halogeno-lower alkyl, lower alkyl, hydroxy, lower alkoxy, lower alkoxyalkoxy, lower alkenyl, lower alkynyl, amino, alkylamino, alkoxyamino, cycloalkyl, cycloalkenyl, aryl, lower aryl, heterocyclyl or lower heterocyclyl;

$R_4$, and $R_5$ are each independently selected from H, halogen, halogeno-lower alkyl, lower alkyl, lower alkoxy, t-butyl-OC—(=O)-benzyl-OC(=O)— or $CH_3C$(=O)—; $R_4$ and $R_5$ form a 4-6 membered saturated ring as a heterocyclyl with their attached nitrogen;

$R_6$ is selected from H, halogen, halogeno-lower alkyl, lower alkyl;

W and Z are each independently selected from O, S, N—R or CH—R;

G is selected from C—R, C—(CN) or N;

a and c are each independently selected from 0, 1 or 2;

b is selected from 1, 2 or 3;

ring Q is defined in claim 1;

or a pharmaceutically acceptable salt thereof.

4. The method according to claim 1, comprising administering an effective amount of a compound of Formula II

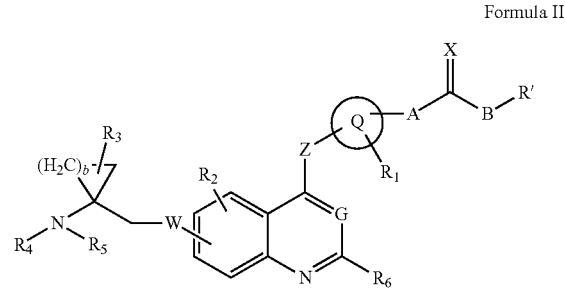

Formula II wherein
R is

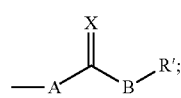

A is selected from direct bond or —N(R')—;

B is selected from direct bond, —N(R')—, —C(=X)— or —C(=)N(R')—;

X is selected from O or S;

R' is selected from H, halogen, halogeno-lower alkyl, lower alkyl, aryl or heterocyclyl;

W and Z are each independently selected from O or N—R;

G is selected from C—R, or N;

$R_1$, $R_2$ and $R_3$ are each independently selected from H, halogen, halogeno-lower alkyl, lower alkyl, hydroxy, lower alkoxy;

$R_4$ and $R_5$ are each independently selected from H, halogen, halogeno-lower alkyl, lower alkyl, hydroxy, lower alkoxy, lower alkoxyalkoxy, lower alkenyl, lower alkynyl, lower alkyl-OC(=O)—, ary-OC(=O)—, aryl lower alkylenyl-OC(=O)—, lower alkyl-C(=O)—, ary-C(=O)— or aryl lower alkylenyl-C(=O)—;

$R_6$ is H or F;

b is selected from 1, 2 or 3;

ring Q is defined in claim 1;

or a pharmaceutically acceptable salt thereof.

5. The method according to claim 1, comprising administering an effective amount of a compound of Formula III

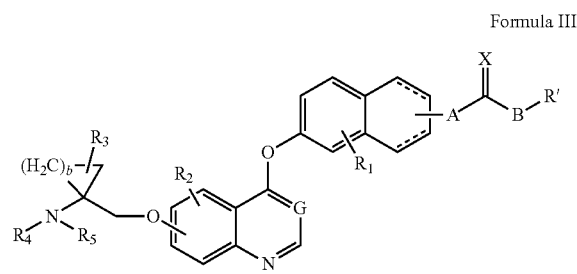

Formula III wherein
R is:

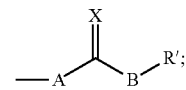

A is selected from direct bond or —N(R')—;

B is selected from —N(R')—, —C(=X)— Or —C(=X)N(R')—;

R' is selected from H, halogen, halogeno-lower alkyl, lower alkyl, aryl or heterocyclyl;

X is selected from O or S

G is selected from C—R, or N;

$R_1$, $R_2$ and $R_3$ are each independently selected from H, halogen, halogeno-lower alkyl, lower alkyl, hydroxy, lower alkoxy;

$R_4$ and $R_5$ are each independently selected from H, halogen, halogeno-lower alkyl, lower alkyl, hydroxy, lower alkoxy, lower alkoxyalkoxy, lower alkenyl, lower alkynyl, lower alkyl-OC(=O)—, ary-OC(=O)—, aryl lower alkylenyl-OC(=O)—, lower alkyl-C(=O)—, ary-C(=O)— or aryl lower alkylenyl-C(=O)—;

b is selected from 1, 2 or 3;

or a pharmaceutically acceptable salt thereof.

6. The method according to claim 1, comprising administering an effective amount of a compound of Formula IV

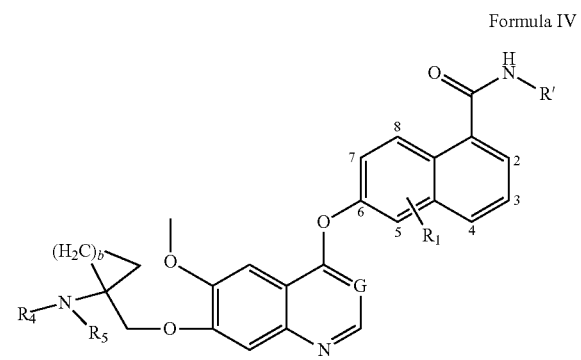

Formula IV wherein

R₁ is selected from H or 5-F;

R₄ is H or CH₃;

R₅ is selected from H, CH₃, CH₃CO—, BzlOCO— or t-BuOCO—;

b is selected from 1, 2 or 3;

G is CH or N;

R' is selected from the following groups: H, CH₃,

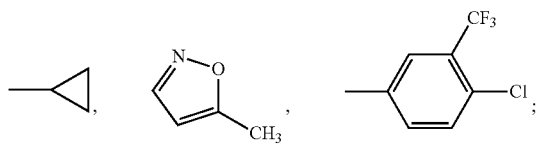

or a pharmaceutically acceptable salt thereof.

7. The method according to claim 1, comprising administering an effective amount of a compound of Formula V Formula V

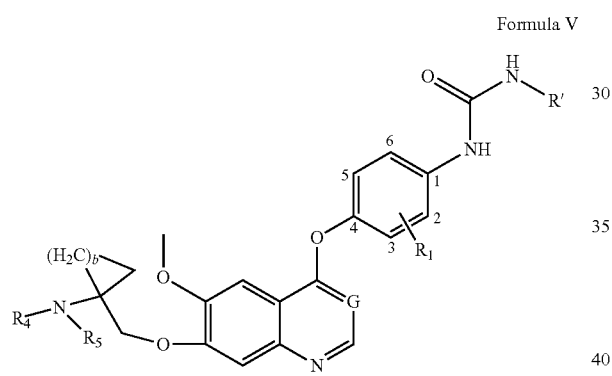

wherein

R₁ is selected from H, 3-F or 2-Cl;

R₄ is H or CH₃

R₅ is elected from H, CH₃, CH₃CO—, BzlOCO— or t-BuOCO—;

b is selected from 1, 2 or 3;

G is CH or N;

R' is selected from the following groups: H, CH₃,

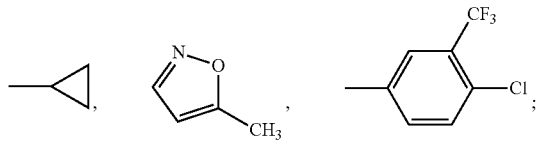

or a pharmaceutically acceptable salt thereof.

8. The method according to claim 1, comprising administering an effective amount of a compound selected from the group consisting of

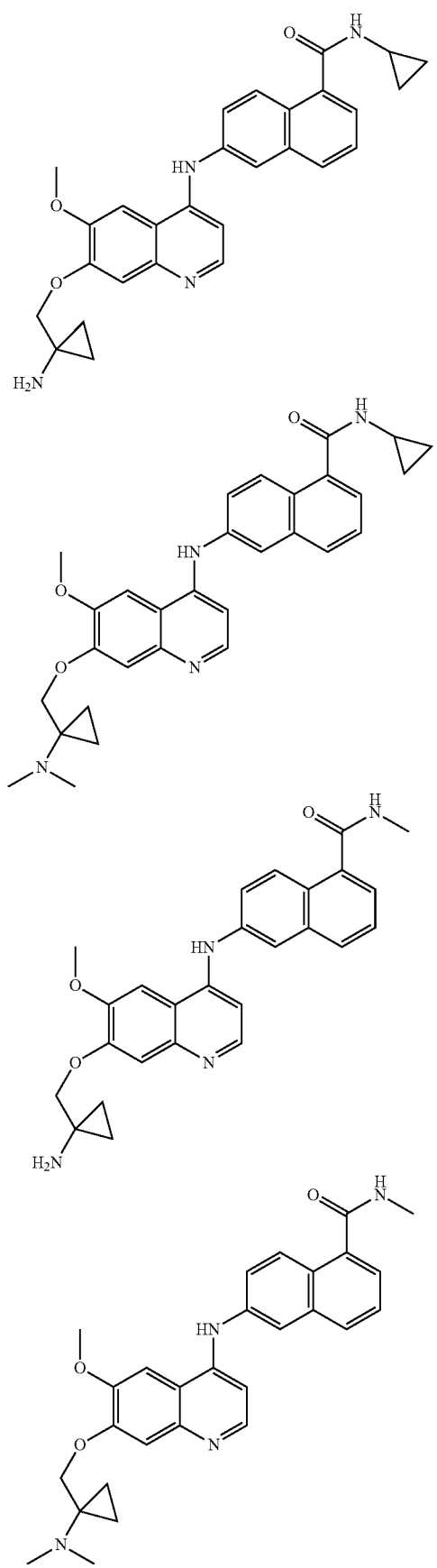

49
-continued
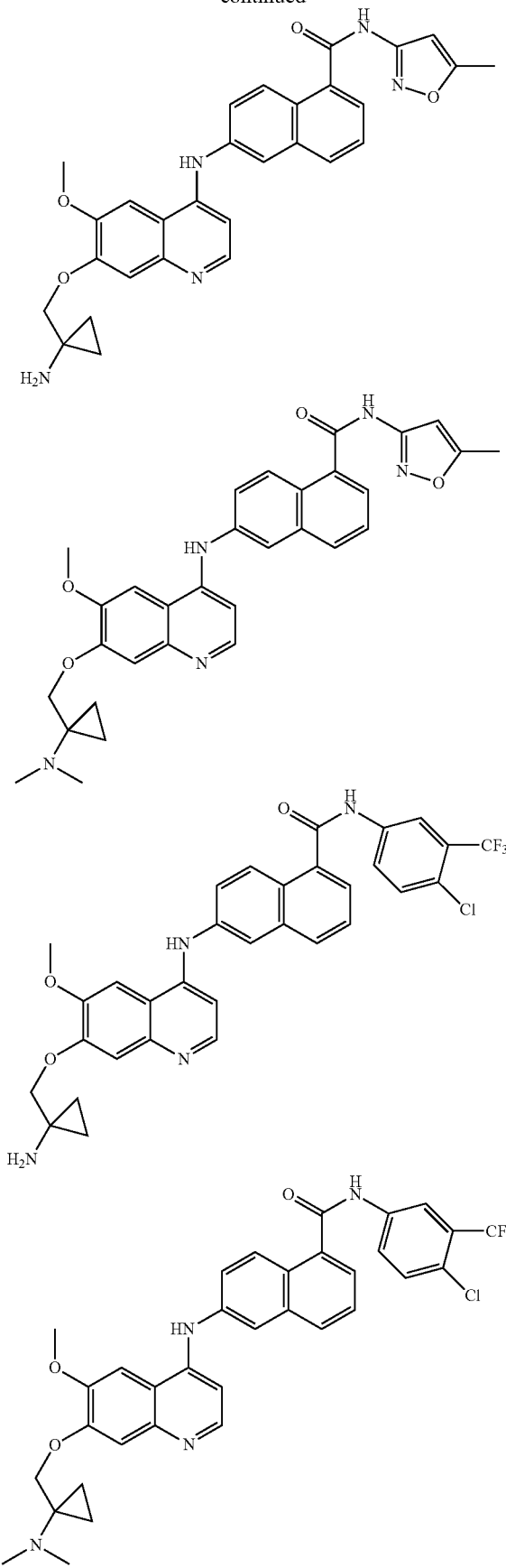
50
-continued
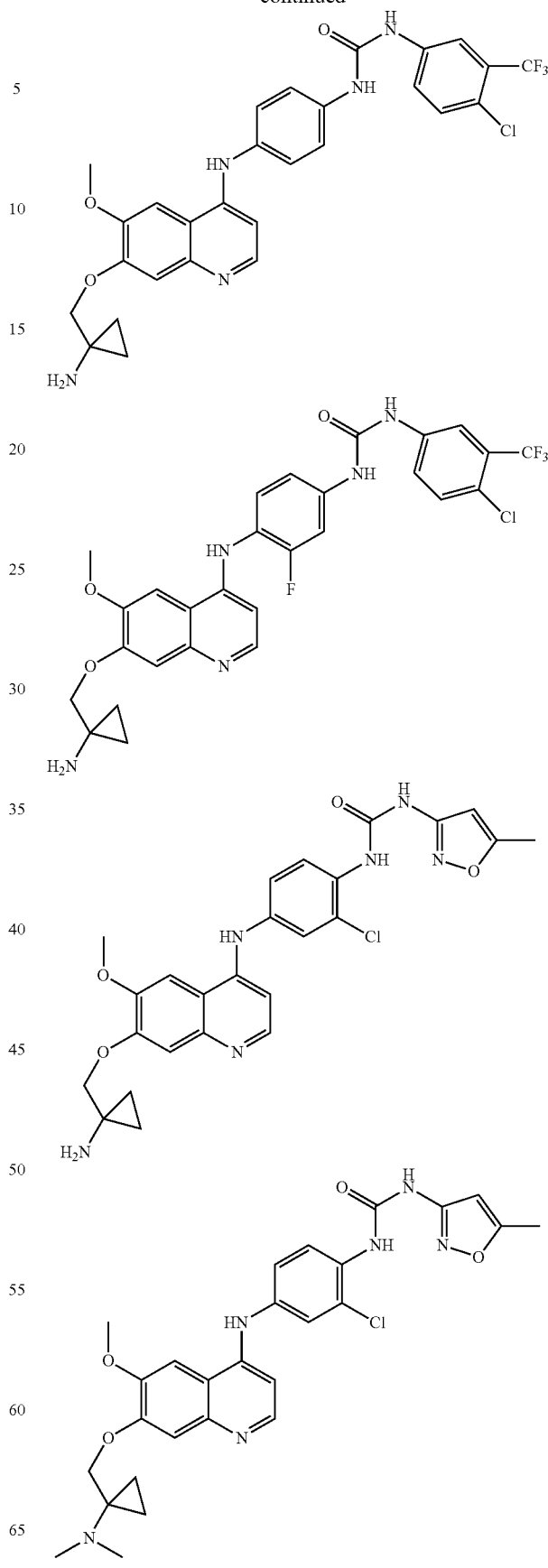

51
-continued
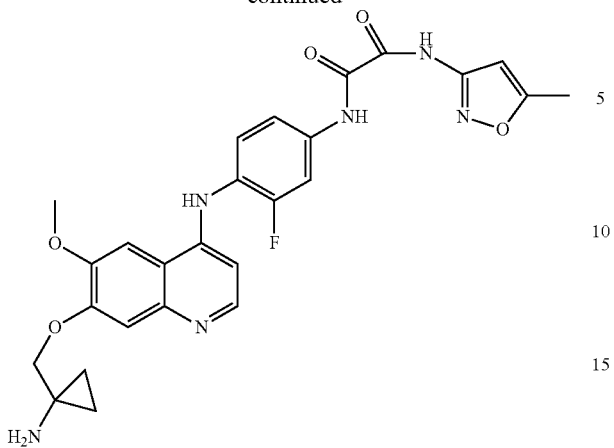
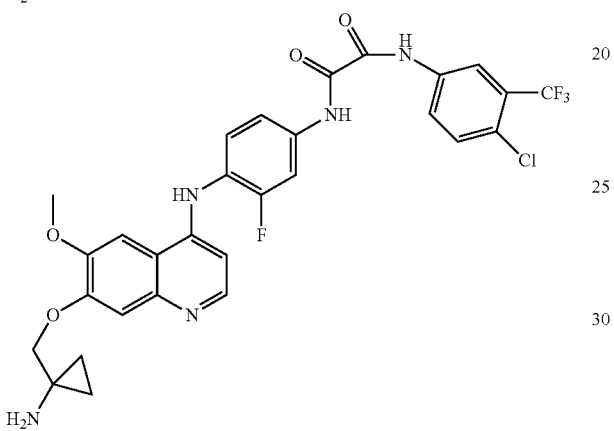
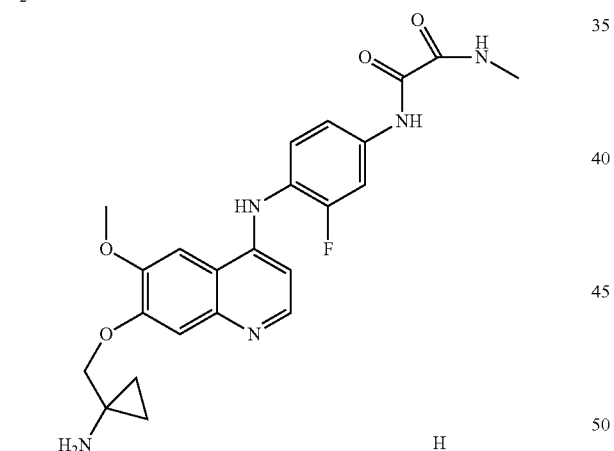
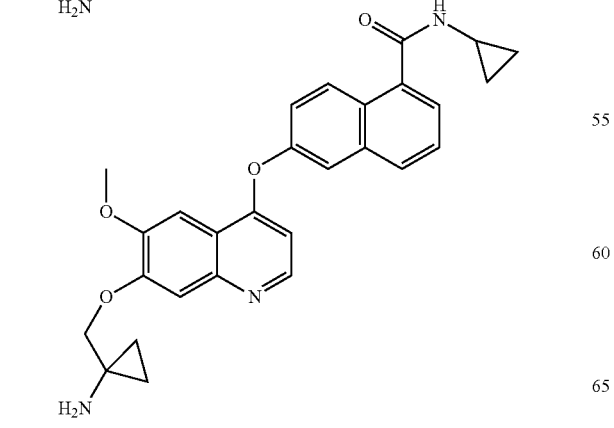
52
-continued
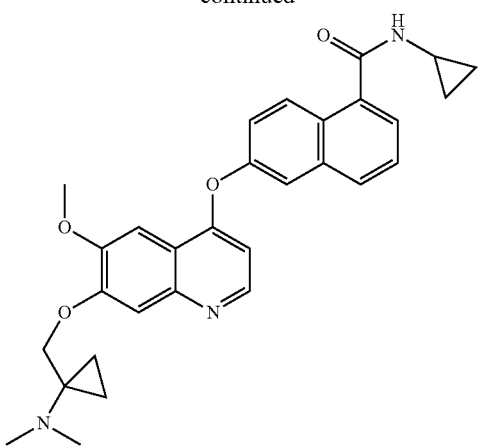
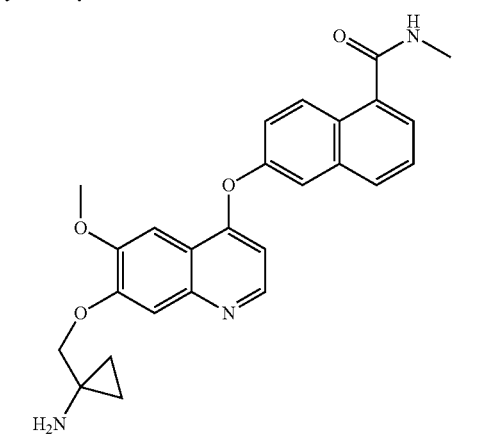
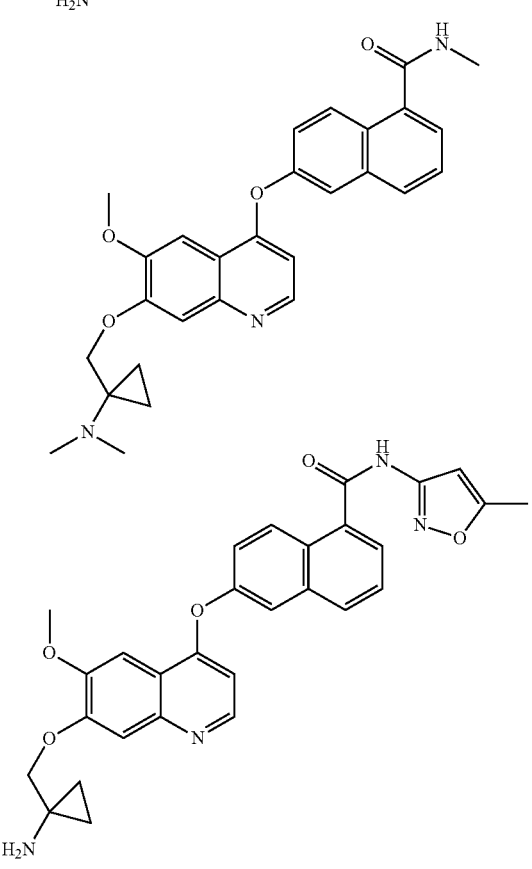

53
-continued
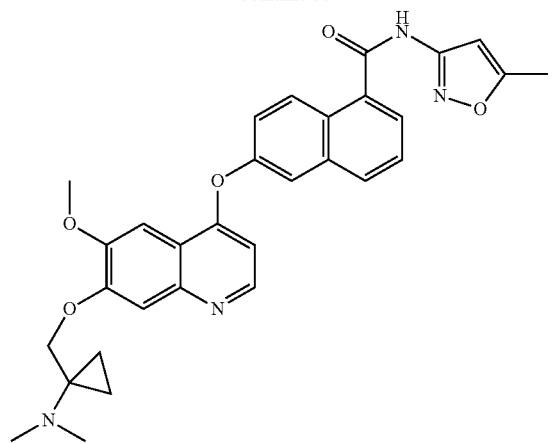
54
-continued
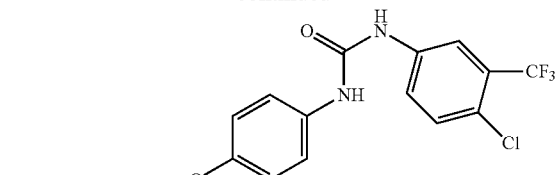
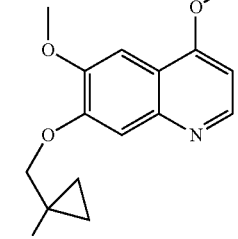
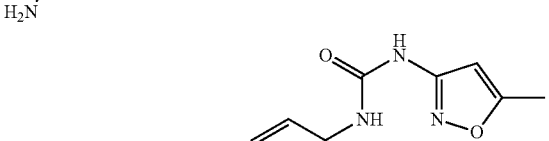
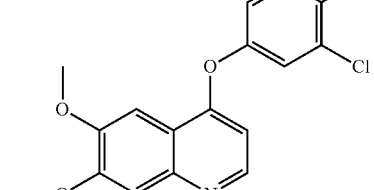
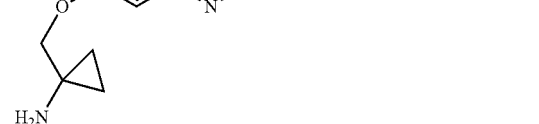
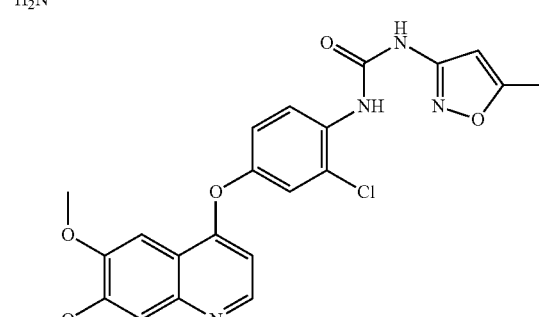
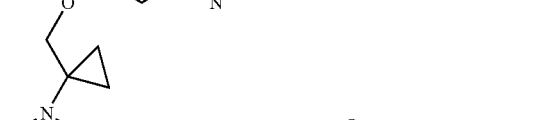
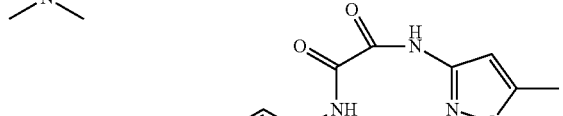
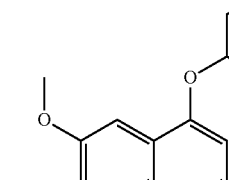

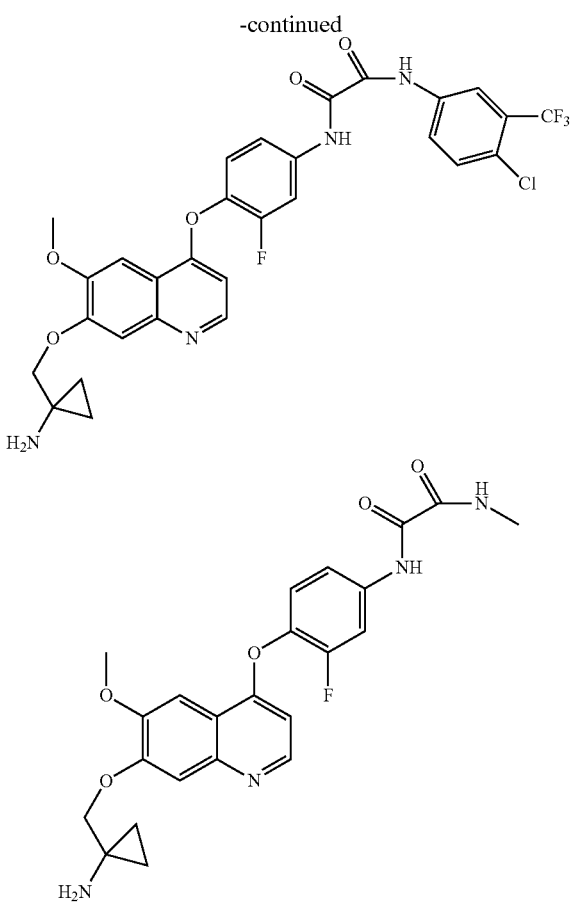

or a pharmaceutically acceptable salt thereof.

9. The method according to claim 1, comprising administering an effective amount of a compound selected from the group consisting of:

Benzyl 1-((6-methoxy-4-(5-(methylcarbamoyl)naphthalen-2-yloxy)quinolin-7-yloxy)methyl)cyclopropylcarbamate
Benzyl 1-((4-(5-(cyclopropylcarbamoyl)naphthalen-2-yloxy)-6-methoxyquinolin-7-yloxy)methyl)-cyclopropylcarbamate
6-(7-((1-Aminocyclopropyl)methoxy)-6-methoxyquinolin-4-yloxy)-N-methyl-1-naphthamide
6-(7-((1-(Dimethylamino)cyclopropyl)methoxy)-6-methoxyquinolin-4-yloxy)-N-methyl-1-naphthamide
6-(7-((1-Aminocyclopropyl)methoxy)-6-methoxyquinolin-4-yloxy)-N-cyclopropyl-1-naphthamide
N-cyclopropyl-6-(7-((1-(dimethylamino)cyclopropyl)methoxy)-6-methoxyquinolin-4-yloxy)-1-naphth
6-(7-((1-Aminocyclopropyl)methoxy)-6-methoxyquinolin-4-yloxy)-N-(5-methylisoxazol-3-yl)-1-naphthamide
6-(7-((1-(Dimethylamino)cyclopropyl)methoxy)-6-methoxyquinolin-4-yloxy)-N-(5-methylisoxazol-3-yl)-1-naphthamide
6-(7-((1-Aminocyclopropyl)methoxy)-6-methoxyquinolin-4-yloxy)-N-(3-methylisoxazol-5-yl)-1-naphthamide
6-(7-((1-(Dimethylamino)cyclopropyl)methoxy)-6-methoxyquinolin-4-yloxy)-N-(3-methylisoxazol-5-yl)-1-naphthamide
6-(7-((1-Aminocyclopropyl)methoxy)-6-methoxyquinolin-4-yloxy)-N-(4-chloro-3-(trifluoromethyl)-phenyl)-1-naphthamide
N-(4-chloro-3-(trifluoromethyl)phenyl)-6-(7-((1-(dimethylamino)cyclopropyl)methoxy)-6-methoxy-quinolin-4-yloxy)-1-naphthamide
6-(7-((1-(Cyclopropylmethylamino)cyclopropyl)methoxy)-6-methoxyquinolin-4-yloxy)N-methyl-1-naphthamide
6-(7-((1-Cyclopropylmethyl)(methy)amino)cyclopropyl)methoxy)-6-methoxyquinolin-4-yloxy)-N-methyl-1-naphthamide
N-cyclopropyl-6-(7-((1-cyclopropylmethylamino)cyclopropyl)methoxy)-6-methoxyquinolin-4-yloxy)-1-naphthamide
N-cyclopropyl-6-(7-((1-((cyclopropylmethyl)(methyl)amino)cyclopropyl)methoxy)-6-methoxyquinolin-4-yloxy)-1-naphthamide
N-(4-chloro-3-(trifluoromethyl)phenyl)-6-(7-((1-cyclopropylmethyl(methyl)amino)cyclopropyl)-methoxy)-6-methoxyquinolin-4-yloxy)-1-naphthamide
N-(4-chloro-3-(trifluoromethyl)phenyl)-6-(7-((1-((cyclopropylmethyl) (methyl)amino)cyclopropyl)-methoxy)-6-methoxyquinolin-4-yloxy)-1-naphthamide
6-(7-((1-(Cyclopropylmethylamino)cyclopropyl)methoxy)-6-methoxyquinolin-4-yloxy)-N-(5-methylisoxazol-3-yl)-1-naphthamide
6-(7-((1-((Cyclopropylmethyl) (methyl)amino)cyclopropyl)methoxy)-6-methoxyquinolin-4-yloxy)-N-(5-methylisoxazol-3-yl)-1-naphthamide
1-(4-(7-((1-Aminocyclopropyl)methoxy)-6-methoxyquinolin-4-yloxy)-3-fluorophenyl)-3-(4-chloro-3-(trifluoromethyl)phenyl)urea
1-(4-Chloro-3-(trifluoromethyl)phenyl)-3-(4-(7-((1-(dimethylamino)cyclopropyl)methoxy)-6-methoxy-quinolin-4-yloxy)-3-fluorophenyl)urea
1-(4-(7-((1-Aminocyclopropyl)methoxy)-6-methoxyquinolin-4-yloxy)-3-fluorophenyl)-3-(5-methyl-isoxazol-3-yl)urea
1-(4-(7-((1-(Dimethylamino)cyclopropyl)methoxy)-6-methoxyquinolin-4-yloxy)-3-fluorophenyl)-3-(5-methylisoxazol-3-yl)urea
1-(4-(7-((1-Aminocyclopropyl)methoxy)-6-methoxyquinolin-4-yloxy)-2-chlorophenyl)-3-(4-chloro-3-(trifluoromethyl)phenyl)urea
1-(4-Chloro-3-(trifluoromethyl)phenyl)-3-(2-chloro-4-(7-((1-(dimethylamino)cyclopropyl)methoxy)-6-methoxyquinolin-4-yloxy)phenyl)urea
1-(4-(7-((1-Aminocyclopropyl)methoxy)-6-methoxyquinolin-4-yloxy)-2-chlorophenyl)-3-(5-methyl-isoxazol-3-yL)urea
1-(2-Chloro-4-(7-((1-(dimethylamino)cyclopropyl)methoxy)-6-methoxyquinolin-4-yloxy)phenyl)-3-(5-methylisoxazol-3-yl)urea or a pharmaceutically acceptable salt thereof.

10. The method according to claim 1, wherein the compound of formula I is administered as a pharmaceutical composition that comprises as an active ingredient a compound of formula I or a pharmaceutically acceptable salt of the compound and a pharmaceutically acceptable carrier.

11. A method for inhibiting angiogenesis in a subject, said method comprising administering an effective amount of a compound of formula I to a patient in need of such treatment Formula I

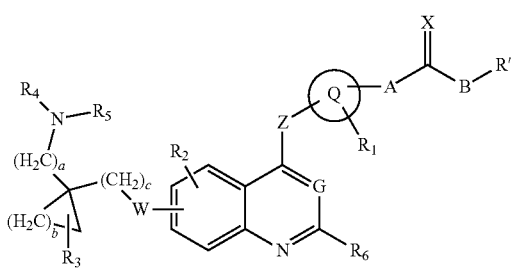

wherein
R is

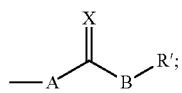

A is selected from direct bond or —N(R')—;
B is selected from direct bond, O, —N(R')—, —C(=X)— —C(=X)N(R')—, lower alkylenyl-C(=X)— or lower alkylenyl-C(=X)N(R')—;
X is selected from O or S;
R' is selected from H, halogen, halogeno-lower alkyl, lower alkyl, hydroxy, lower alkoxy, lower alkoxyalkoxy, lower alkenyl, lower alkynyl, amino, alkylamino, alkoxyamino, cycloalkyl, cycloalkenyl, aryl, lower aryl, heterocyclyl or lower heterocyclyl;
$R_1$, $R_2$ and $R_3$ are each independently selected from H, halogen, halogeno-lower alkyl, lower alkyl, hydroxy, lower alkoxy, lower alkoxyalkoxy, lower alkenyl, or lower alkynyl;
$R_4$ and $R_5$ are each independently selected from H, halogen, halogeno-lower alkyl, lower alkyl, hydroxy, lower alkoxy, lower alkoxyalkoxy, lower alkenyl, lower alkynyl, lower alkyl-OC(=O)—, aryl-OC(=O)—, aryl lower alkylenyl-OC(=O)—, lower alkyl-C(=O)—, aryl-C(=O)—, aryl lower alkylenyl-C(=O)—, lower alkyl-SO$_2$—, ary-SO$_2$—, aryl lower alkylenyl-SO$_2$—, lower alkyl-C(=O)—, aryl-C(=O)—, aryl lower alkylenyl-C(=O)—, lower alkyl-N(R)C(=O)—, aryl-N(R)C(=O)—, or ary lower alkylenyl-N(R)C(=O)—; $R_4$ and $R_5$ connect together to form a 3-8 membered saturated or unsaturated ring with their attached nitrogen;
$R_6$ is selected from H, halogen, halogeno-lower alkyl, lower alkyl;
W and Z are each independently selected from O, S, N—R or CH—R;
G is selected from C—R, C—(CN) or N;
a and c are each independently selected from 0, 1, 2, 3 or 4;
b is selected from 1, 2, 3, 4 or 5; and
ring Q is selected from following groups:

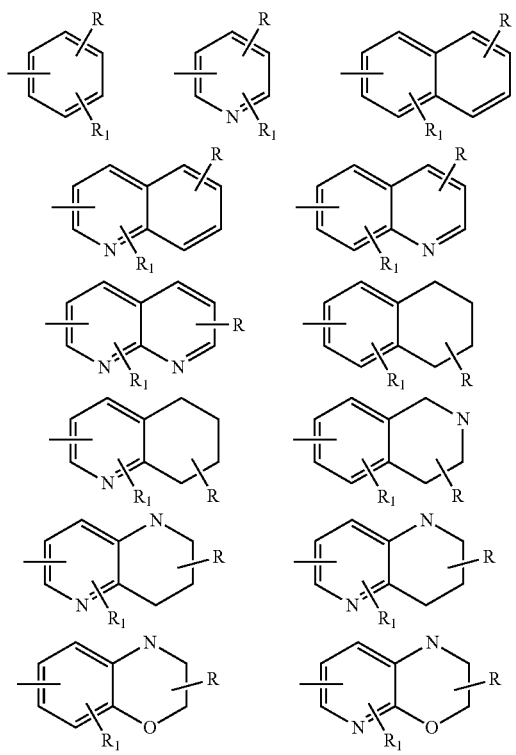

or a pharmaceutically acceptable salt thereof.

* * * * *